(12) United States Patent
Kufe et al.

(10) Patent No.: US 9,044,421 B2
(45) Date of Patent: Jun. 2, 2015

(54) TREATING MUC1-EXPRESSING CANCERS WITH COMBINATION THERAPIES

(71) Applicants: GENUS ONCOLOGY, LLC., Vernon Hills, IL (US); DANA-FARBER CANCER INSTITUTE, INC., Boston, MA (US)

(72) Inventors: Donald Kufe, Wellesley, MA (US); Surender Kharbanda, Natick, MA (US)

(73) Assignees: Genus Oncology, LLC, Vernon Hills, IL (US); Dana-Farber Cancer Institute, Inc., Boston, MA (US)

(*) Notice: Subject to any disclaimer, the term of this patent is extended or adjusted under 35 U.S.C. 154(b) by 0 days.

(21) Appl. No.: 13/852,390

(22) Filed: Mar. 28, 2013

(65) Prior Publication Data
US 2013/0274198 A1 Oct. 17, 2013

Related U.S. Application Data

(60) Provisional application No. 61/616,804, filed on Mar. 28, 2012, provisional application No. 61/780,409, filed on Mar. 13, 2013.

(51) Int. Cl.
| | |
|---|---|
| *A61K 38/03* | (2006.01) |
| *A61P 35/00* | (2006.01) |
| *A61K 31/5377* | (2006.01) |
| *A61K 45/06* | (2006.01) |
| *A61K 38/08* | (2006.01) |
| *A61K 38/17* | (2006.01) |

(52) U.S. Cl.
CPC ............. *A61K 38/03* (2013.01); *A61K 31/5377* (2013.01); *A61K 45/06* (2013.01); *A61K 38/08* (2013.01); *A61K 38/1735* (2013.01)

(58) Field of Classification Search
CPC ... A61K 38/03; A61K 31/5377; A61K 45/06; A61K 38/08; A61K 38/1735; A61K 2300/00
See application file for complete search history.

(56) References Cited

U.S. PATENT DOCUMENTS

| | | | |
|---|---|---|---|
| 5,595,756 A | 1/1997 | Bally et al. |
| 5,912,232 A | 6/1999 | Talmadge |
| 6,261,569 B1 | 7/2001 | Comis et al. |
| 6,548,643 B1 | 4/2003 | McKenzie et al. |
| 7,118,862 B2 | 10/2006 | Kufe et al. |
| 7,183,059 B2 | 2/2007 | Verdine et al. |
| 7,192,713 B1 | 3/2007 | Verdine et al. |
| 7,247,297 B2 | 7/2007 | Weichselbaum et al. |
| 7,556,935 B2 | 7/2009 | Kufe et al. |
| 7,576,057 B2 | 8/2009 | Scribner et al. |
| 7,589,170 B1 | 9/2009 | Smythe et al. |
| 7,705,012 B2 | 4/2010 | Pisano et al. |
| 2002/0044943 A1 | 4/2002 | Longenecker et al. |
| 2002/0086829 A1 | 7/2002 | Gefter |
| 2005/0042209 A1 | 2/2005 | Kufe et al. |
| 2005/0053606 A1 | 3/2005 | Kufe et al. |
| 2005/0089957 A1 | 4/2005 | Goddard et al. |
| 2005/0271650 A1 | 12/2005 | Freimark et al. |
| 2005/0282744 A1 | 12/2005 | Holingsworth et al. |
| 2006/0293234 A1 | 12/2006 | Schroeder |
| 2007/0071675 A1 | 3/2007 | Wu et al. |
| 2007/0105767 A1 | 5/2007 | Kharbanda et al. |
| 2007/0202134 A1 | 8/2007 | Kufe et al. |
| 2007/0207209 A1 | 9/2007 | Murphy et al. |
| 2008/0286264 A1 | 11/2008 | Kufe |
| 2009/0047307 A1 | 2/2009 | Harrop et al. |
| 2009/0087437 A1 | 4/2009 | Kufe |
| 2009/0092600 A1 | 4/2009 | Kufe |
| 2009/0098054 A1 | 4/2009 | Kufe |
| 2009/0136520 A1 | 5/2009 | Kufe |
| 2009/0232812 A1 | 9/2009 | Kufe et al. |
| 2009/0326192 A1 | 12/2009 | Nash et al. |
| 2010/0125055 A1 | 5/2010 | Kufe et al. |
| 2011/0015138 A1 | 1/2011 | Kufe et al. |
| 2011/0251246 A1 | 10/2011 | Kufe et al. |
| 2012/0045502 A1 | 2/2012 | Kufe et al. |
| 2012/0172312 A1 | 7/2012 | Kufe et al. |
| 2013/0039974 A1 | 2/2013 | Kufe et al. |

FOREIGN PATENT DOCUMENTS

| | | |
|---|---|---|
| EP | 1538164 | 6/2005 |
| WO | WO 00/34468 | 6/2000 |
| WO | WO 01/18035 | 3/2001 |
| WO | WO 01/57068 | 8/2001 |

(Continued)

OTHER PUBLICATIONS

Alpha-1A-adrenergic receptor—*Homo sapiens*, from http://www.ncbi.nlm.nih.gov/protein/AAA35496.1, p. 1, accessed Jun. 11, 2014.*
Chalhoub et al, PTEN and the PI3-Kinase Pathway in Cancer, Annu. Rev. Pathol. Mech. Dis., 2009, 4, pp. 127-150.*
PTEN—*Homo sapiens*, from http://www.ncbi.nlm.nih.gov/protein/NP_000305.3, pp. 1-5, accessed Jun. 12, 2014.*
Kato et al, Phosphoinositide 3-kinase is activated by MUC1 but not responsible for MUC1-induced suppression of Toll-like receptor 5 signaling, Am J Physiol Lung Cell Mol Physiol, 2007, 293, pp. L686-L692.*

(Continued)

*Primary Examiner* — Julie Ha
*Assistant Examiner* — Li Ni Komatsu
(74) *Attorney, Agent, or Firm* — Parker Highlander PLLC

(57) ABSTRACT

The invention provides method of treating cancers that express mucin 1 (MUC1) by the administration of phosphatidylinositol 3-kinase (PI3-K) inhibitors in combination with MUC1-directed cancer therapies. The PI3-K inhibition may advantageously be combined with peptides that inhibit MUC1 oligomerization, or further with other standard anti-cancer therapies such as chemo-, radio- and surgical therapies.

15 Claims, 10 Drawing Sheets

(56) References Cited

FOREIGN PATENT DOCUMENTS

| WO | WO 2005/101021 | 10/2005 |
|---|---|---|
| WO | WO 2008/121767 | 10/2008 |

OTHER PUBLICATIONS

Clark et al, Constitutive and Inducible Akt Activity Promotes Resistance to Chemotherapy, Trastuzumab, or Tamoxifen in Breast Cancer Cells, Molecular Cancer Therapeutics, 2002, 1, pp. 707-717.*
Definition of inhibitor, from http://www.merriam-webster.com/medical/inhibitor, p. 1, accessed Jun. 12, 2014.*
Abe and Kufe, "Structural analysis of the DF3 human breast carcinoma-associated protein," *Cancer Res.*, 49(11):2834-2839, 1989.
Agata et al., "MUC1 oncoportein blocks death receptor-mediated apoptosis by inhibiting recruitment of caspase-8," *Cancer Res.*, 68(15):6136-6144, 2008.
Ahmad et al., "MUC1 oncoprotein activates the IkappaB kinase beta complex and constitutive NF-kappaB signalling," *Nat. Cell Biol.*, 9:1419-1427, 2007.
Ahmad et al., "MUC1-C oncoprotein functions as a direct activator of the nuclear factor-κβ p65 transcription factor," *Cancer Research*, 69: 7013-21, 2009.
Ahmad et al., "MUC1-C oncoprotein promotes STAT3 activation in an autoinductive regulatory loop," *Sci. Signal.*, 4(160):ra9, Feb. 15, 2011.
Ahmad et al., "Triterpenoid CDDO-Me blocks the NF-kappaB pathway by direct inhibition of IKKbeta on Cys-179," *J. Biol. Chem.*, 281:35764-9, 2006.
Anderson et al., "Multiple myeloma: New insights and therapeutic approaches," *Hematology*, 1:147-165, 2000.
Arkin et al., "Structural aspects of oligomerization taking place between the transmembrane a-helices of bitopic membrane proteins," *Biochimica et Biophysica Acta*, 1565(2):347-363, 2002.
Auerbach et al., "Angiogenesis assays: Problems and pitfalls," *Cancer and Metastasis Reviews*, 19(1-2):167-172, 2000.
Baldus et al., "MUC1 and nuclear beta-catenin are coexpressed at the invasion front of colorectal carcinomas and are both correlated with tumor prognosis," *Clin. Cancer Res.*, 10(8):2790-2796, 2004.
Beatty et al., "Cutting edge: Transgenic expression of human MUC1 in IL-10 −/− Mice accelerates inflammatory bowel disease and progression to colon cancer,", *J. Immunol..*, 179(2):735-739, 2007.
Begum et al., "Muc1 based breast cancer vaccines: role of post translational modifications," *J. Ayub. Med. Coll. Abbottabad.*, 20(4):130-133, 2008.
Bitler et al., "Intracellular MUC1 peptides inhibit cancer progression," *Clin. Canc. Res.*, 15(1):100-109, 2009.
English Translation of Office Communication issued in corresponding Chinese Patent Application 200980149998.9, dated Mar. 4, 2013.
Fischer, "Cellular uptake mechanisms and potential therapeutic utility of peptidic cell delivery vectors: Progress 2001-2006," *Medicinal Research Reviews*, 27(6):755-795, 2007.
Gura, "Systems for identifying new drugs are often faulty," *Science*, 278:1041-1042, 1997.
Hodel et al., "The three-dimensional structure of the autoproteolytic, nuclear pore-targeting domain of the human nucleoporin Nup98,"*Mol. Cell*, 10(2):347-358, 2002.
Hruby, "Designing peptide receptor agonists and antagonists," *Nature Reviews. Drug Discovery*, 1(11):847-858, 2002.
Hu et al., "MUC1 cytoplasmic tail: a potential therapeutic target for ovarian cancer," *Future Drugs*, 6(8):1261-1271, 2006.
Huang et al., "MUC1 cytoplasmic domain coactivates Wnt target gene transcription and confers transformation," *Cancer Biol. Ther.*, 2(6):702-706, 2003.
Huang et al., "MUC1 oncoprotein blocks glycogen synthase kinase 3beta-mediated phosphorylation and degradation of beta-catenin," *Cancer Res.*, 65(22):10413-10422, 2005.
International Search Report and Written Opinion issued in International application No. PCT/US11/24760, dated May 27, 2011.
Jain, "Barriers to drug delivery in solid tumors," *Scientific American*, 58-65, 1994.

Joshi et al., "MUC1 oncoprotein is a druggable target in human prostate cancer cells," *Mol. Cancer Ther.*, 8(11):3056-3065, 2009.
Kau et al., "Nuclear transport and cancer: from mechanism to intervention," *Nat. Rev. Cancer*, 4(2):106-17, 2004.
Kawano et al., "MUC1 oncoprotein promotes growth and survival of human multiple myeloma cells," *International Journal of Oncology*, 33(1):153-159, 2008.
Khodarev et al., "Cooperativity of the MUC1 oncoprotein and STAT1 pathway in poor prognosis human breast cancer," *Oncogene*, 29(6):920-9, 2009.
Kinlough et al., "Recycling of MUC1 is dependent on its palmitoylation," *The Journal of Biological Chemistry*, 281(17):12112-12122, 2006.
Kufe et al., "Differential reactivity of a novel monoclonal antibody (DF3) with human malignant versus benign breast tumors," *Hybridoma*, 3(3):223-232, 1984.
Kufe, "Functional targeting of the MUC1 oncogene in human cancers," *Cancer Biology & Therapy*, 8(13):1197-1203, 2009.
Kufe, "Human MUC1 oncoprotein is of functional importance fo the development of prostate cancer," Award No. W81XWH-08-1-0093, Annual Report, prepared for U.S. Army Medical Research and Materiel Command, Mar. 2009.
Kufe, "Mucins in cancer: function, prognosis and therapy," *Nat. Rev. Cancer*, 9(12):874-885, 2009.
Kufe, "Targeting the human MUC1 oncoprotein: a tale of two proteins," *Cancer Biol. Ther.*, 7(1):81-84, 2008.
Leng et al., "Nuclear import of the MUC1-C oncoprotein is mediated by nucleoporin Nup62," *The Journal of Biological Chemistry*, 282(27):19321-19330, 2007.
Levitin et al., "The MUC1 SEA module is a self-cleaving domain," *J. Biol. Chem.*, 280(39):33374-33386, 2005.
Li and Cozzi, "MUC1 is a promising therapeutic target for prostate cancer therapy," *Current Cancer Drugs Targets*, 7(3):259-271, 2007.
Li et al., "DF3/MUC1 Signaling in Multiple Myeloma Cells is Regulated by Interleukin-7," *Cancer Biol. Ther.*, 2(2):37-43, 2003.
Li et al., "Heregulin targets gamma-catenin to the nucleolus by a mechanism dependent on the DF3/MUC1 oncoprotein," *Mol. Cancer Res.*, 1(10):765-775, 2003.
Li et al., "Human DF3/MUC1 carcinoma-associated protein functions as an oncogene," *Oncogene*, 22 (38): 6107-6110, 2003.
Li et al., "Interaction of glycogen synthase kinase 3beta with the DF3/MUC1 carcinoma-associated antigen and beta-catenin," *Mol. Cell Biol.*, 18(12):7216-7224, 1998.
Li et al., "The c-Src tyrosine kinase regulates signaling of the human DF3/MUC1 carcinoma-associated antigen with GSK3 beta and beta-catenin," *J. Biol. Chem.*, 276(9):6061-6064, 2001.
Li et al., "The epidermal growth factor receptor regulates interaction of the human DF3/MUC1 carcinoma antigen with c-Src and beta-catenin," *J. Biol. Chem.*, 276(38):35239-35242, 2001.
Ligtenberg et al., "Cell-associated episialin is a complex containing two proteins derived from a common precursor," *J. Biol. Chem.*, 267 (9), 6171-6177, 1992.
Ling et al. "MUC1 C-terminal Heterodimer and Its Tumorgenicity," *Progress in Biochemistry and Biophysics*, 34(4): 375-381, 2007. (English translation of Chinese publication).
Macao, "Autoproteolysis coupled to protein folding in the SEA domain of the membrane-bound MUC1 mucin," *Nat. Struct. Mol. Biol.*, 13 (1), 71-76, 2006.
Mukherjee et al., "Progression of pancreatic adenocarcinoma is significantly impeded with a combination of vaccine and COX-2 inhibition," *J. Immunol.*, 182(1):216-224, 2009.
National Cancer Institute—Types of Leukemia, published Nov. 25, 2008. Accessed online at http:/www.cancer.gov/cancertopoics/wyntk/leukemia/page3 on Apr. 12, 2013.
Notice of Allowance (Corrected Notice of Allowability) issued in United States. U.S. Appl. No. 12/789,127, dated Mar. 6, 2013.
Notice of Allowance issued in U.S. Appl. No. 12/789,127, dated Jan. 23, 2012.
Office Action issued in European Patent Application No. 09740811.6, dated Jun. 22, 2012.
Office Communication issued in Australian Patent Application No. 2010253834, dated Mar. 8, 2013.

(56) References Cited

OTHER PUBLICATIONS

Office Communication issued in U.S. Appl. No. 12/580,865, dated Dec. 27, 2011.
Office Communication issued in U.S. Appl. No. 12/580,865, dated May 24, 2012.
Office Communication issued in U.S. Appl. No. 12/580,865, dated Nov. 2, 2012.
Office Communication issued in U.S. Appl. No. 12/789,127, dated Mar. 28, 2012.
Office Communication issued in U.S. Appl. No. 12/789,127, dated Jul. 5, 2012.
PCT International Search Report and Written Opinion, issued in International patent Application No. PCT/US10/36436, dated Oct. 19, 2010.
PCT International Search Report and Written Opinion, issued in International application No. PCT/US2009/061051, dated Nov. 26, 2010.
Pearce et al., "Chapter 18.2 Failure Modes in the Discovery Process," Neidle, Stephen, Ed. In: *Cancer Drug Design and Discovery*. Elsevier/Academic Press, pp. 427-431, 2008.
Peczuh et al., "Peptide and protein recognition by designed molecules," *Chem. Rev.*, 100:2479-2494, 2000.
Raina et al., "Abstract 2243: Targeting the MUC1-C oncoprotein synergistically enhances cytotoxicity of breast carcinoma cells in combination with PI3K inhibitors," [abstract] In: Proceedings of the 103rd Annual Meeting of the American Association for Cancer Research; Mar. 31-Apr. 4, 2012; Chicago, IL. Philadelphia (PA): AACR; Cancer Res 2012; 72(8 Suppl): Abstract nr 2243. doi:1538-7445.AM2012-2243.
Raina et al., "Dependence on the MUC1-C oncoprotein in non-small cell lung cancer cells," *Mol. Cancer Ther.*, 10(5):806-816, 2011. E-published Mar. 18, 2011. Doi:10.1158/1535-7163.mct-10-1050.
Raina et al., "Direct targeting of the mucin 1 oncoprotein blocks survival and tumorigenicity of human breast carcinoma cells," *Cancer Res.*, 69 (12): 5133-5141, 2009.
Raina et al., "MUC1 oncoprotein blocks nuclear targeting of c-Abl in the apoptotic response to DNA damage," *EMBO J.*, 25(16):3774-3783, 2006.
Raina et al., "The MUC1 oncoprotein activates the anti-apoptotic phosphoinositide 3-kinase/Akt and Bcl-xL pathways in rat 3Y1 fibroblasts," *J. Biol. Chem.*, 279 (20):20607-20612, 2004.
Ramasamy et al., "The MUC1 and galectin-3 oncoproteins function in a microRNA-dependent regulatory loop," *Mol. Cell*, 27 (6):992-1004, 2007.
Ren et al., "Human MUC1 carcinoma-associated protein confers resistance to genotoxic anticancer agents," *Cancer Cell*, 5 (2):163-175, 2004.
Ren et al., "MUC1 oncoprotein functions in activation of fibroblast growth factor receptor signaling," *Mol. Cancer Res.*, 4 (11): 873-883, 2006.
Ren et al., "MUC1 oncoprotein is targeted to mitochondria by heregulin-induced activation of c-Src and the molecular chaperone HSP90," *Oncogene*, 25 (1):20-31, 2006.
Ren et al., "Protein kinase C delta regulates function of the DF3/MUC1 carcinoma antigen in beta-catenin signaling," *J. Biol. Chem.*, 277 (20):17616-17622, 2002.
Response to Office Communication issued in U.S. Appl. No. 12/789,127, dated Apr. 30, 2012.
Response to Office Communication issued in U.S. Appl. No. 12/789,127, dated Jan. 4, 2013.
Response to Office Communication issued in U.S. Appl. No. 12/580,865, dated Feb. 23, 2012.
Response to Office Communication issued in U.S. Appl. No. 12/580,865, dated Sep. 24, 2012.
Response to Office Communication issued in U.S. Appl. No. 12/580,865, dated Feb. 4, 2013.
Schroeder et al., "MUC1 overexpression results in mammary gland tumorigenesis and prolonged alveolar differentiation," *Oncogene*, 23 (34):5739-5747, 2004.
Schroeder et al., "Transgenic MUC1 interacts with epidermal growth factor receptor and correlates with mitogen-activated protein kinase activation in the mouse mammary gland," *J. Biol. Chem.*, 276(16):13057-13064, 2001.
Shepherd et al., "Modular alpha-helical mimetics with antiviral activity against respiratory syncitial virus," *JACS*, 128(40):13284-13289, 2006.
Spicer et al., "Molecular cloning and analysis of the mouse homologue of the tumor-associated mucin, MUC1, reveals conservation of potential O-glycosylation sites, transmembrane, and cytoplasmic domains and a loss of minisatellite-like polymorphism," *The Journal of Biological Chemistry*, 226(23):15099-15109, 1991.
Sporn and Suh, "Chemoprevention of cancer," *Carcinogenesis*, 21:525-530, 2000.
Supplementary European Search Report issued in European Patent Application No. 10781227.3, dated Dec. 3, 2012.
Truscott et al., "A J-protein is an essential subunit of the presequence translocase-associated protein import motor of mitochondria," *J. Cell Biol.*, 163(4):707-713, 2003.
Tsutsumida et al., "RNA interference suppression of MUC1 reduced the growth rate and metastatic phenotype of human pancreatic cancer cells," *Clin. Cancer Res.*, 12(10):2976-2987, 2006.
Vermeer et al., "Segregation of receptor and ligand regulates activation of epithelial growth factor receptor," *Nature*, 422(6929):322-6, 2003.
Wei et al., "Human MUC1 oncoprotein regulates p53-responsive gene transcription in the genotoxic stress response," *Cancer Cell*, 7 (2):167-178, 2005.
Wei et al., "MUC1 oncoprotein stabilizes and activates estrogen receptor alpha," *Mol. Cell.*, 21 (2): 295-305, 2006.
Weis, "Regulating access to the genome: nucleocytoplasmic transport throughout the cell cycle," *Cell*, 112(4):441-51, 2003.
Wen et al., "Nuclear association of the cytoplasmic tail of MUC1 and beta-catenin," *J. Biol. Chem.*, 278 (39):38029-38039, 2003.
Yamamoto et al., "Interaction of the DF3/MUC1 breast carcinoma-associated antigen and beta-catenin in cell adhesion," *J. Biol. Chem.*, 272 (19):12492-12494, 1997.
Yin et al., "Human MUC1 carcinoma antigen regulates intracellular oxidant levels and the apoptotic response to oxidative stress," *J. Biol. Chem.*, 278 (37):35458-35464, 2003.
Yin et al., "MUC1 oncoprotein activates the FOXO3a transcription factor in a survival response to oxidative stress," *J. Biol. Chem.*, 279 (44):45721-45727, 2004.
Yin et al., "MUC1 oncoprotein promotes autophagy in a survival response to glucose deprivation," *Int. J. Oncol.*, 34 (6): 1691-1699, 2009.
Yin et al.,"MUC1-C oncoprotein suppresses reactive oxygen species-induced terminal differentiation of acute myelogenous leukemia cells," *Blood*, 117(18):4863-4870, 2011. E-published Mar. 21, 2011. DOI:10.1182/blood-2010-296632.
Yin et al., "Mucin 1 oncoprotein blocks hypoxia-inducible factor 1alpha activation in a survival response to hypoxia," *J. Biol. Chem.*, 282 (1):257-266, 2007.
Yin et al., "Survival of human multiple myeloma cells is dependent on MUC1 C-terminal transmembrane subunit oncoprotein function," *Mol. Pharmacol.*, 78(2):166-174, 2010.
Young et al., "Molecular chaperones Hsp90 and Hsp70 deliver preproteins to the mitochondrial import receptor Tom70," *Cell.* 112 (1): 41-50, 2003.
Zhou et al., "MUC1 oncoprotein is a target for small molecule inhibitors," *Molecular Pharmacology*, Published online before print Feb. 23, 2011, Doi: 10.1124/mol.110.070797.
Raina et al., "Targeting the MUC1-C oncoprotein synergistically enhances cytotoxicity of breast carcinoma cells in combination with PI3K inhibitors," poster presented at American Association for Cancer Research 103rd Annual Meeting, Chicago, IL (US), Mar. 31-Apr. 4, 2012.

* cited by examiner

MUC1-CD

CQCRRKNYGQLDIFPARDTYHPMSEYPTYHTHGRYVPPSSTDRSPYEKVSAGNGGSSLYTNPAVAAASL
(SEQ ID NO:65)

|  |  |  | SEQ ID NOS: |
|---|---|---|---|
| Endogenous | A I V Y L I A L A V C Q C R R K N Y G |  | 51 |
| GO-200-1B | Ac-A I V Y L-*S5*-A L A-*S5*-C Q C-R-R K N Y G-NH2 |  | 52 |
| GO-200-2B | Ac-A K K Y L-*S5*-A L A-*B5*-C Q C-*S5*-R K N Y  NH2 |  | 53 |
| GO-201 | *NH2-[dR]$_9$-* C Q C R R K N Y G Q L D I F P *–COOH* | TFA | 54 |
| GO-202 | *NH2-[dR]$_9$-* C Q C R R K N *–COOH* | TFA | 55 |
| GO-203 | *NH2-[dR]$_9$- dC dQ dC dR dR dK dN-COOH* | TFA | 55 |
| GO-203-1 | *Acetyl- [dR]$_9$ - dC dQ dC dR dR dK dN  NH2* | TFA | 55 |
| GO-203-2 | *Acetyl- [dR]$_9$ - dC dQ dC dR dR dK dN  NH2* | HCL | 55 |
| GO-203a | *NH2-dR- dR- dR - dC dQ dC dR dR dK dN dR -COOH* | TFA | 56 |
| GO-203b | *NH2-dR- dR- dC dQ dC dR dR dK dN dR -COOH* | TFA | 57 |
| GO-203c | *Acetyl-dR- dR - dC dQ dC dR dR dK dN- NH2* | TFA | 58 |
| GO-203-cyc | *Acetyl- [dR]$_9$ - dC dQ dC dR dR dK dN  NH2* | TFA | 55 |
| GO-203-cyc-1 | *Acetyl-dR- dR - dC dQ dC dR dR dK dN- NH2* | TFA | 58 |
| GO-204 | *NH2- dC dQ dC dR dR dK dN-[dR]9 -COOH* | TFA | 59 |
| GO-205 | *Acetyl- [dR]$_9$ - dN dK dR dR dC dQ dC –NH2* | TFA | 60 |
| GO-206 | *NH2- dN dK dR dR dC dQ dC--[dR]9 -COOH* | TFA | 61 |
| GO-207 | *NH2-[dR]$_9$- dC dQ dC dR dR dK -COOH* | TFA | 4 |
| GO-208 | *NH2-[dR]$_9$- dC dQ dC dR dR -COOH* | TFA | 50 |
| GO-209 | *NH2-[dR]$_9$- dC dQ dC dR -COOH* | TFA | 49 |
| GO-210 | *NH2-[dR]$_9$- dC dQ dC-COOH* | TFA | 62 |
| CP-1 | *NH2-[dR]$_9$-* A Q A R R K N Y G Q L D I F P   *COOH* | TFA | 63 |
| CP-2 | *NH2-[dR]$_9$- dA dQ dA dR dR dK dN-COOH* | TFA | 64 |

TREATING MUC1-EXPRESSING CANCERS WITH COMBINATION THERAPIES

The present application claims benefit of priority to U.S. Provisional Application Ser. No. 61/616,804, filed Mar. 28, 2012, and U.S. Provisional Application Ser. No. 61/780,409, filed Mar. 13, 2013, the entire contents of both applications being hereby incorporated by reference.

Pursuant to 37 C.F.R. 1.821(c), a sequence listing is submitted herewith as an ASCII compliant text file named "GENUP0034US_ST25.txt", created on Mar. 28, 2013 and having a size of ~18 kilobytes. The content of the aforementioned file is hereby incorporated by reference in its entirety.

BACKGROUND OF THE INVENTION

1. Field of the Invention

This invention relates to the fields of biology, medicine and oncology. In particular, the invention relates to the use of PI3-K helicase inhibitors to treat MUC1-expressing cancers.

2. Related Art

Mucin 1 (MUC1) is an oncoprotein that is aberrantly overexpressed in human cancers by mechanisms that are not clearly understood (Kufe, 2009). MUC1 consists of two subunits that form a non-covalent complex at the cell membrane (Kufe, 2009). The MUC1 N-terminal (MUC1-N) ectodomain is the mucin component of the heterodimer that contains glycosylated tandem repeats. The transmembrane MUC1 C-terminal subunit (MUC1-C) has a 58 amino acid (aa) extracellular domain that interacts with the epidermal growth factor receptor (EGFR) and other receptor tyrosines (Ramasamy et al., 2007; Kufe, 2009).

The 72 aa MUC1-C cytoplasmic domain binds to PI3-K and contributes to activation of the PI3-K→AKT pathway (Raina et al., 2004; Raina et al., 2011). Overexpression of the MUC1-C subunit, as found in diverse human cancers, is sufficient to induce anchorage-independent growth and tumorigenicity (Li et al., 2003; Huang et al., 2005; Kufe, 2009). Upregulation of MUC1-C also attenuates the induction of cell death in response to genotoxic, oxidative and hypoxic stress (Yin and Kufe, 2003; Ren et al., 2004; Yin et al., 2007). MUC1-C localizes to the nucleus, where it associates with transcription factors, such as NF-κB RelA and STAT3, and promotes activation of their target genes, including MUC1 itself (Ahmad et al., 2009; Ahmad et al., 2011). Thus, MUC1-C contributes, at least in part, to its own overexpression through autoinductive regulatory loops (Kufe, 2009).

Based on these findings, MUC1-C has emerged as an attractive target for cancer treatment using approaches that block its function and thereby overexpression. For example, cell-penetrating peptides and small molecules that inhibit the MUC1-C cytoplasmic domain attenuate localization of MUC1-C to the nucleus of cancer cells and downregulate its overexpression (Raina et al., 2009; Joshi et al., 2009; Zhou et al., 2011). There is, however, limited information about combining anti-MUC1-C therapies with other agents.

SUMMARY OF THE INVENTION

Thus, in accordance with the present invention, there is provided a method of inhibiting a cancer cell that expresses MUC1 comprising contacting said cancer cell with (a) an inhibitor of PI3-K and (b) a MUC1 peptide of at least 4 consecutive MUC1 residues and no more than 20 consecutive MUC1 residues and comprising the sequence CQC, wherein the amino-terminal cysteine of CQC is covered on its NH$_2$-terminus by at least one amino acid residue that need not correspond to the native MUC-1 transmembrane sequence. Inhibiting may, for example, comprise killing the cancer cells, or inhibiting its growth or proliferation. The cancer cell may be metastatic, recurrent or multidrug resistant cancer cell.

The method may further comprise contacting said cancer cell with said PI3-K inhibitor more than once. The method may further comprise contacting said cancer cell with said peptide more than once. The method may further comprise contacting said cancer cell with said PI3-K inhibitor and said peptide more than once. The PI3-K inhibitor may be a PI3-K Class I inhibitor, for example, a PI3-K Class I-selective or PI3-K Class I-specific inhibitor. The cancer cell may be a carcinoma cell, a leukemia cell or a myeloma cell. The carcinoma cell may be a prostate or breast carcinoma cell.

The peptide may comprise at least 5, 6, 7 or 8 consecutive MUC1 residues, comprising CQCRRK (SEQ ID NO:4). The peptide may contain no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1. The peptide may be fused to a cell delivery domain, such as poly-D-R, poly-D-P or poly-D-K. The peptide may comprise all L amino acids or all D amino acids, or a mix of L and D amino acids.

In another embodiment, there is provided a method of treating MUC1-expressing cancer cell in a subject comprising administering to said subject (a) an inhibitor of PI3-K and (b) a MUC1 peptide of at least 4 consecutive MUC1 residues and no more than 20 consecutive MUC1 residues and comprising the sequence CQC, wherein the amino-terminal cysteine of CQC is covered on its NH$_2$-terminus by at least one amino acid residue that need not correspond to the native MUC-1 transmembrane sequence. Treating may, for example, comprise killing the cancer cells, inducing growth arrest of said cancer cell, inhibiting proliferation of said cancer cell inducing apoptosis of said cancer cell and/or necrosis of a tumor tissue comprising said tumor cell. It may also comprises improving patient survival, reducing tumor burden, rendering an unresectable tumor resectable, improving patient comfort or any other relevant clinical parameter. The cancer cell may be metastatic, recurrent or multidrug resistant cancer cell.

The method may further comprise contacting said cancer cell with said PI3-K inhibitor more than once. The method may further comprise contacting said cancer cell with said peptide more than once. The method may further comprise contacting said cancer cell with said PI3-K inhibitor and said peptide more than once. The PI3-K inhibitor may be a PI3-K Class I inhibitor, for example, a PI3-K Class 1-selective or PI3-K Class I-specific inhibitor. The cancer cell may be a carcinoma cell, a leukemia cell or a myeloma cell. The carcinoma cell may be a prostate or breast carcinoma cell.

The peptide may comprise at least 5, 6, 7 or 8 consecutive MUC1 residues, comprising CQCRRK (SEQ ID NO:4). The peptide may contain no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1. The peptide may be fused to a cell delivery domain, such as poly-D-R, poly-D-P or poly-D-K. The peptide may comprise all L amino acids or all D amino acids, or a mix of L and D amino acids.

The method may further comprise administering to said subject an additional anti-cancer therapy, such as surgery, chemotherapy, radiotherapy, hormonal therapy, toxin therapy, immunotherapy, and cryotherapy. The additional anti-cancer therapy may be administered prior to said PI3-K inhibitor and said peptide, after said PI3-K inhibitor and said peptide, or at the same time as said PI3-K inhibitor and/or said peptide. Administering may comprise intravenous, intra-arterial, intra-tumoral, subcutaneous, topical or intraperitoneal administration, and/or may comprises local, regional (e.g., into tumor vasculature), systemic, or continual administration. The subject may be a human.

The PI3-K inhibitor may be administered at 0.1-500 mg/kg/d, or at 10-100 mg/kg/d. The PI3-K inhibitor and/or said peptide may be administered daily. The PI3-K inhibitor and/or said peptide may be administered daily for 7 days, 2 weeks, 3 weeks, 4 weeks, one month, 6 weeks, 8 weeks, two months, 12 weeks, or 3 months. The PI3-K inhibitor and/or said peptide may be administered weekly. The PI3-K inhibitor and/or said peptide may be administered weekly for 2 weeks, 3 weeks, 4 weeks, 6 weeks, 8 weeks, 10 weeks, or 12 weeks.

The method may further comprise, prior to administering, the step of assessing MUC1 expression in a cancer cell from said subject. The assessing may comprise MUC1 nucleic acid detection or MUC protein detection. Also provided is a kit comprising (a) a PI3-K inhibitor and (b) and MUC1 peptide of at least 4 consecutive MUC1 residues and no more than 20 consecutive MUC1 residues and comprising the sequence CQC, wherein the amino-terminal cysteine of CQC is covered on its $NH_2$-terminus by at least one amino acid residue that need not correspond to the native MUC-1 transmembrane sequence. Further provided is a use of a PI3-K inhibitor and a MUC1 peptide in the treatment of MUC1-expressing cancer.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed.

(FIG. 6A) Isobologram analysis for ZR-75-1 cells treated with GO-203-2C and LY294002. (FIG. 6B) Combination index calculated using the CALCUSYN® Software (analyzer of combined drug efficacy).

(FIG. 7A) Isobologram analysis for ZR-75-1 cells treated with GO-203-2C and GDC-0941. (FIG. 7B) Combination index calculated using the CALCUSYN® Software (analyzer of combined drug efficacy).

FIG. 10. MUC-1 peptide sequences.

DESCRIPTION OF ILLUSTRATIVE EMBODIMENTS

Figure 1:
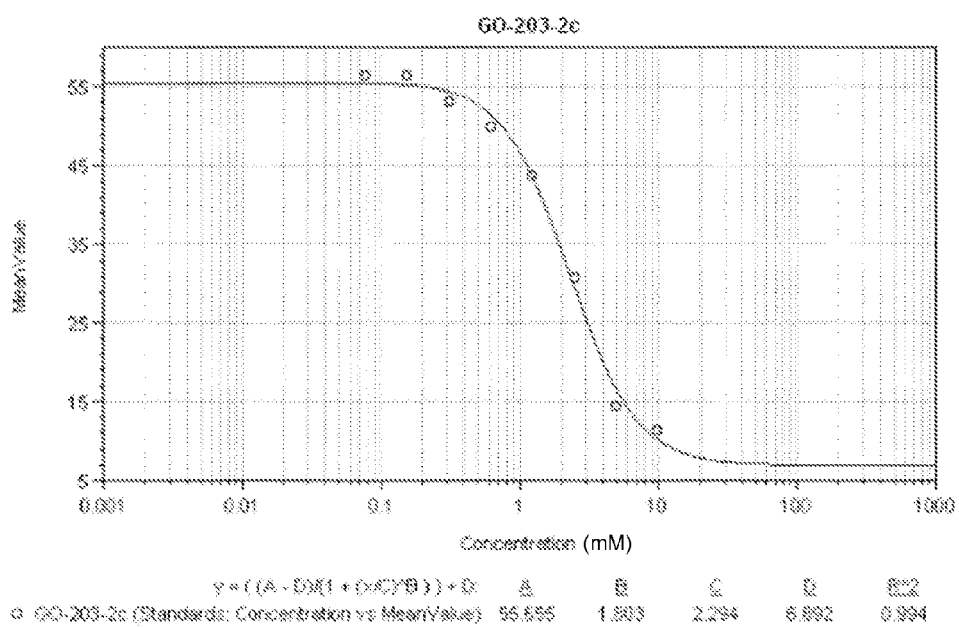
FIG. 1. H-1650 non small cell lung carcinoma cells in a 96-well plate were treated with various concentrations of purified GO-203-2C for four days. AlamarBlue dye was added to the cells on day 5, and the absorbance was measured at 570 and 600 nm. A 4-parameter curve was obtained by plotting the percentage reduction of alamarBlue calculated using these absorbance values against the concentration of GO-203-2C used.
Figure 2:
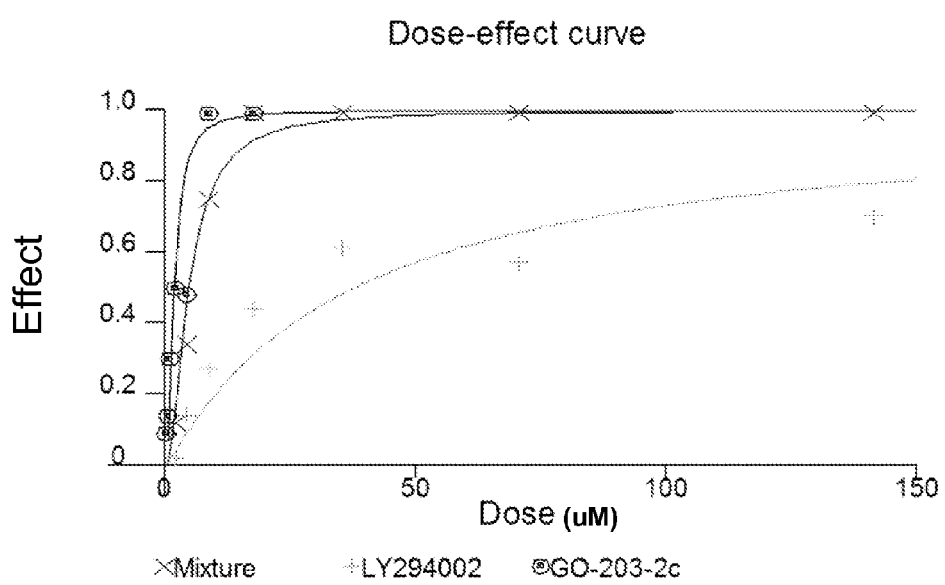
FIG. 2. Dose-response curve for ZR-75-1 breast carcinoma cells treated with GO-203-2C and LY294002 either alone or in combination.
Figure 3:
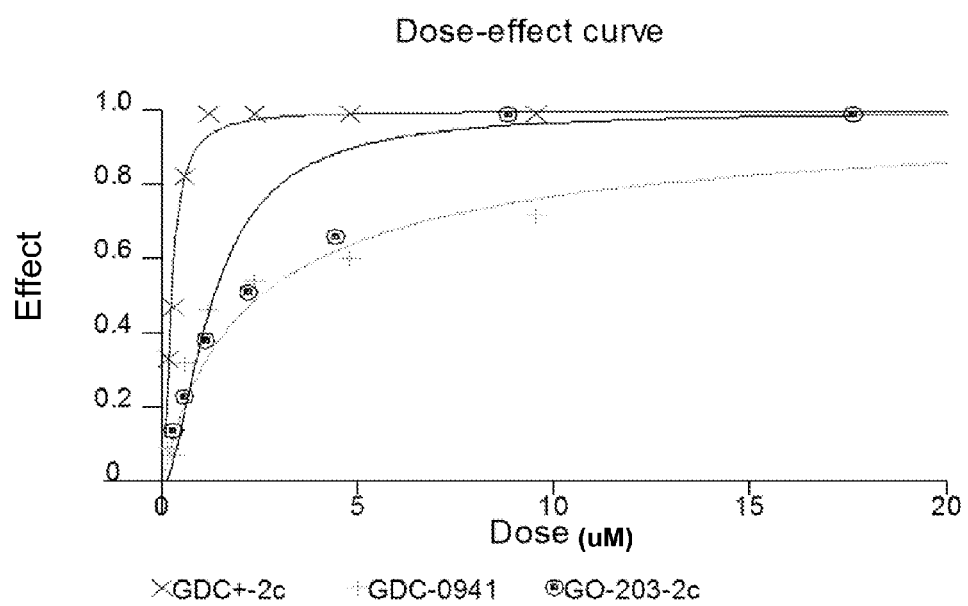
FIG. 3. Dose-response curve for ZR-75-1 breast carcinoma cells treated with GO-203-2C and GDC-0941 either alone or in combination.
Figure 4:
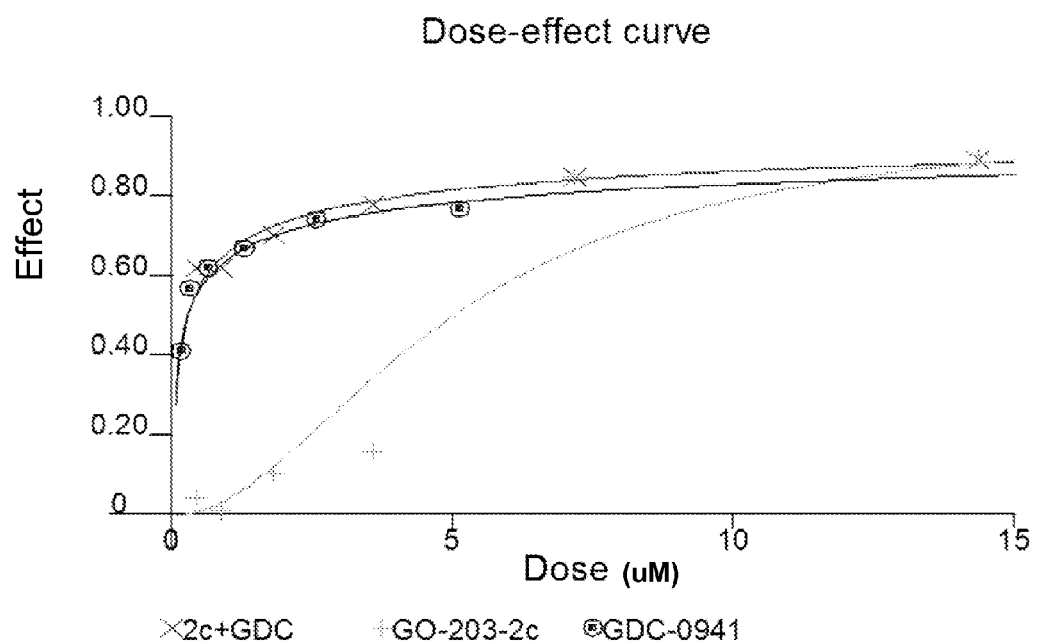
FIG. 4. Dose-response curve for MCF-7 breast carcinoma cells treated with GO-203-2C and GDC-0941 either alone or in combination.
Figure 5:
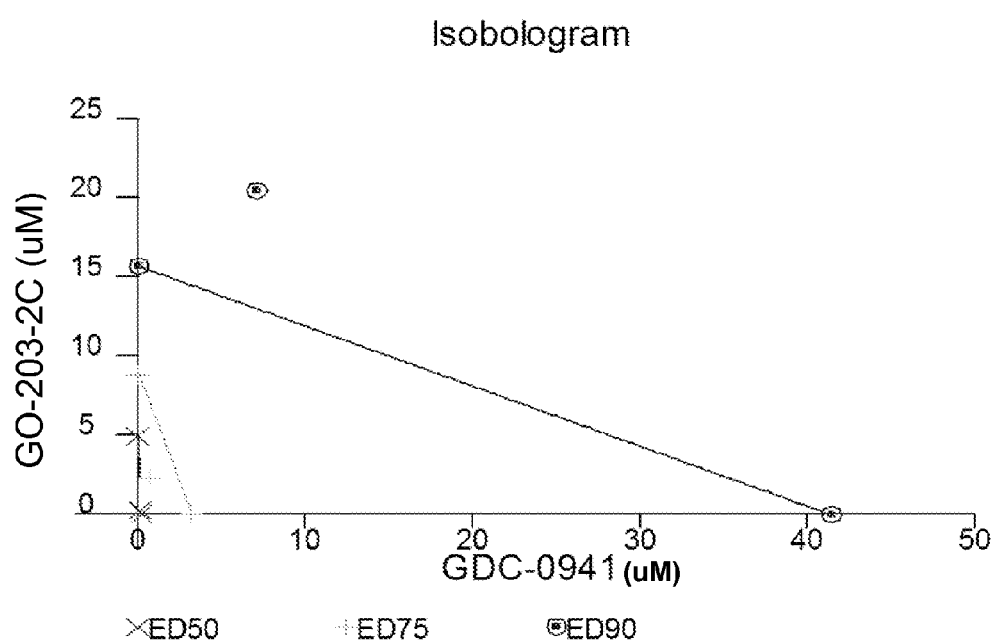
FIG. 5. Isobolograms of MCF-7 breast carcinoma cells treated with GO-203-2C and GDC-0941 alone or in combination.
Figure 6A:
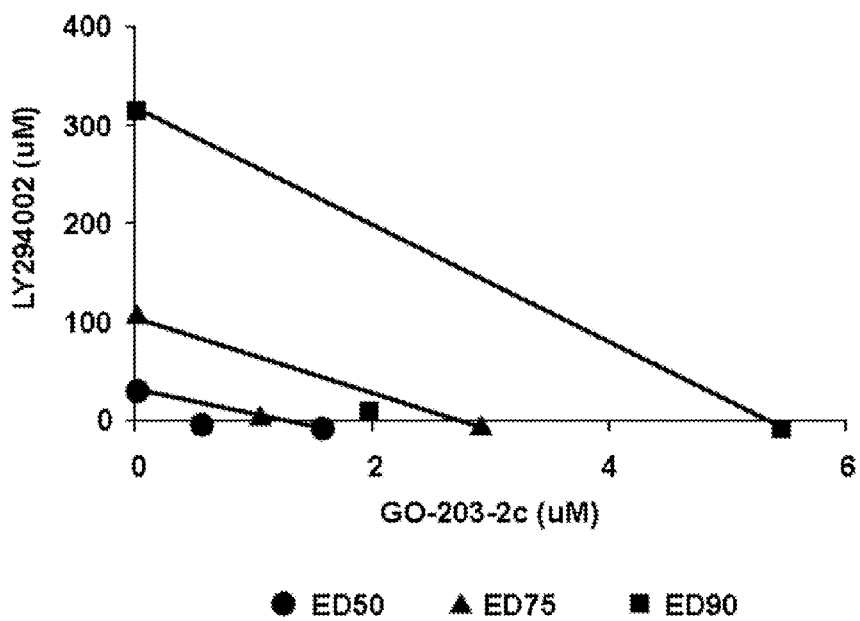
FIGS. 6A-B.
Figure 6B:
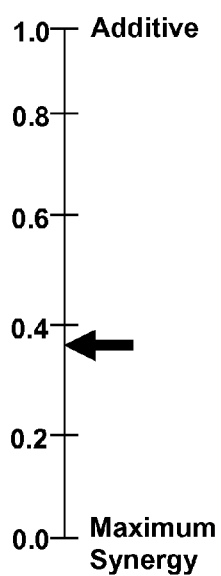
Figure 7A:
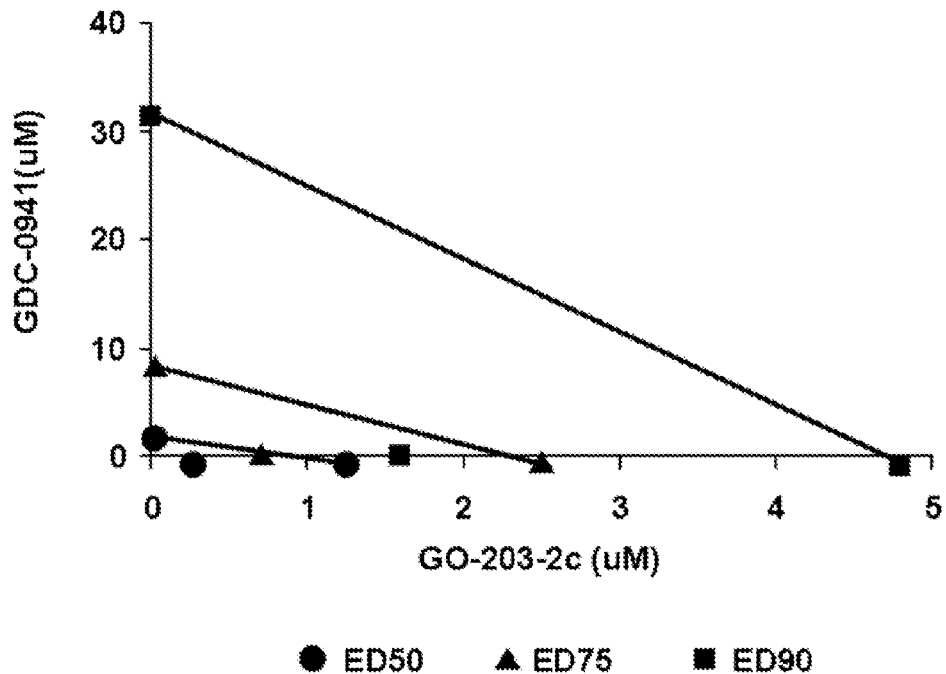
FIGS. 7A-B.
Figure 7B:
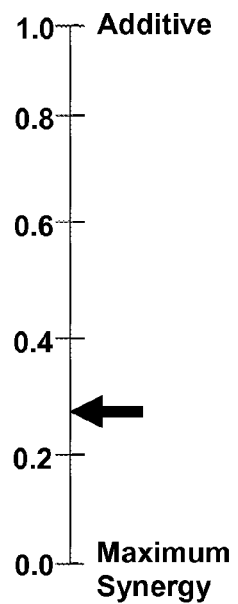
Figure 8:
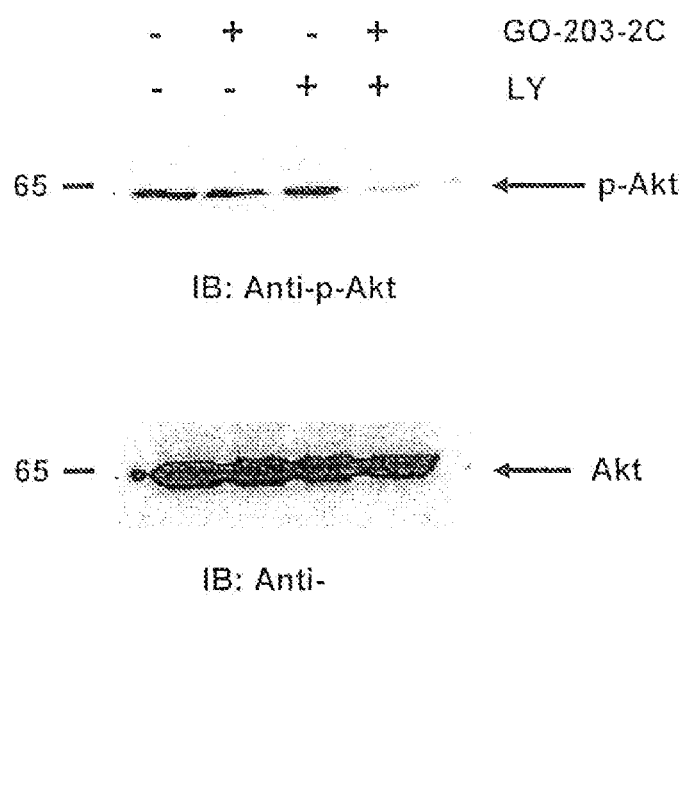
FIG. 8. ZR-75-1 breast carcinoma cells were treated with GO-203-2C and LY294002 either alone or in combination. Total cell lysates were prepared and analyzed by immunoblotting with anti-phospho-AKT (top panel) or anti-AKT (bottom panel).
Figure 9:
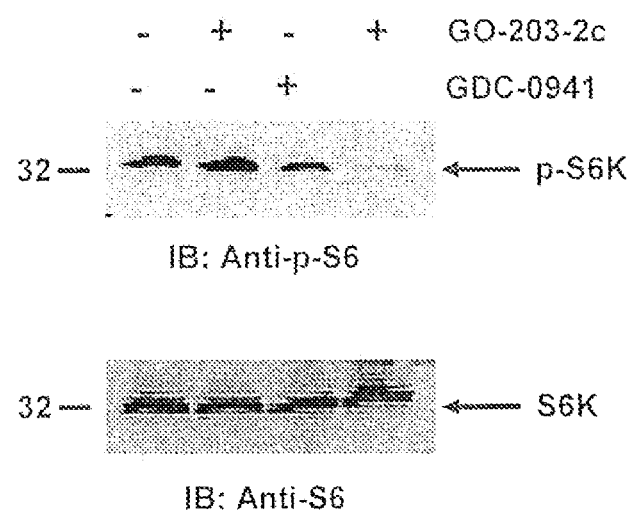
FIG. 9. ZR-75-1 breast carcinoma cells were treated with GO-203-2C and GDC-0941 either alone or in combination. Total cell lysates were prepared and analyzed by immunoblotting with anti-phospho-S6K (top panel) or anti-S6K (bottom panel).

As discussed above, overexpression of the MUC1-C subunit, as found in diverse human cancers, is sufficient to induce anchorage-independent growth and tumorigenicity (Li et al., 2003; Huang et al., 2005; Kufe, 2009). Upregulation of MUC1-C also attenuates the induction of cell death in response to genotoxic, oxidative and hypoxic stress (Yin and Kufe, 2003; Ren et al., 2004; Yin et al., 2007). The 72 as MUC1-C cytoplasmic domain has been shown to bind to PL3-K and contribute to activation of the PI3-K→AKT pathway (Raina et al., 2004; Raina et al., 2011). MUC1-C also localizes to the nucleus, where it associates with transcription factors, such as NF-κB RelA and STAT3, and promotes activation of their target genes, including MUC1 itself (Ahmad et al., 2009; Ahmad et al., 2011). Thus, MUC1-C contributes, at least in part, to its own overexpression through autoinductive regulatory loops (Kufe, 2009).

The inventors have previously used MUC1-C peptide inhibitors that bind to the MUC1-C cytoplasmic domain and block the formation of MUC1-C dimers in breast cancer cells and shown that inhibition of MUC1-C arrests growth and induces necrotic death of the breast carcinoma cells. Here, they demonstrate that combining the MUC1-C inhibitor GO-203-2C with agents that target PI3-K (LY294002, GDC0941) induces highly synergistic cytotoxicity of breast carcinoma cells. Notably, GO-203-2C significantly enhanced the effectiveness of these PI3-K inhibitors by contributing to the downregulation of p-AKT and p-S6K. Taken together, these findings provide support for combining PI3-K inhibitors and GO-203-2C, an agent now undergoing Phase 1 evaluation, to improve treatment of patients with breast cancer. These and other aspects of the invention are described in greater detail below.

I. MUC1

A. Structure

MUC1 is a mucin-type glycoprotein that is expressed on the apical borders of normal secretory epithelial cells (Kufe et al., 1984). MUC1 forms a heterodimer following synthesis as a single polypeptide and cleavage of the precursor into two subunits in the endoplasmic reticulum (Ligtenberg et al., 1992). The cleavage may be mediated by an autocatalytic process (Levitan et al., 2005). The >250 kDa MUC1 N-terminal (MUC1 N-ter, MUC1-N) subunit contains variable numbers of 20 amino acid tandem repeats that are imperfect with highly conserved variations and are modified by O-linked glycans (Gendler et al., 1988; Siddiqui et al., 1988). MUC1-N is tethered to the cell surface by dimerization with the ~23 kDa C-terminal subunit (MUC1 C-ter, MUC1-C), which includes a 58 amino acid extracellular region, a 28 amino acid transmembrane domain and a 72 amino acid cytoplasmic domain (CD; SEQ ID NO:1) (Merlo et al., 1989). The human MUC1 sequence is shown below:

```
                                            (SEQ ID NO: 2)
GSVVVQLTLAFREGTINVHDVETQFNQYKTEAASRYNLTISDVSVSDVPF

PFSAQSGAGVPGWGIALLVLVCVLVALAIVYLIALAVCQCRRKNYGQLDI

FPARDTYHPMSEYPTYHTHGRYVPPSSTDRSPYEKVSAGNGGSSLSYTNP

AVAATSANL
```

The bold sequence indicates the CD, and the underlined portion is an oligomer-inhibiting peptide (SEQ ID NO:3). With transformation of normal epithelia to carcinomas, MUC1 is aberrantly overexpressed in the cytosol and over the entire cell membrane (Kufe et al., 1984; Perey et al., 1992). Cell membrane-associated MUC1 is targeted to endosomes by clathrin-mediated endocytosis (Kinlough et al., 2004). In addition, MUC1-C, but not MUC1-N, is targeted to the nucleus (Baldus et al., 2004; Huang et al., 2003; Li et al., 2003a; Li et al., 2003b; Li et al., 2003c; Wei et al., 2005; Wen et al., 2003) and mitochondria (Ren et al., 2004).

B. Function

MUC1 interacts with members of the ErbB receptor family (Li et al., 2001b; Li et al., 2003c; Schroeder et al., 2001) and with the Wnt effector, β-catenin (Yamamoto et al., 1997). The epidermal growth factor receptor and c-Src phosphorylate the MUC1 cytoplasmic domain (MUC1-CD) on Y-46 and thereby increase binding of MUC1 and β-catenin (Li et al., 2001a; Li et al., 2001b). Binding of MUC1 and β-catenin is also regulated by glycogen synthase kinase 3β and protein kinase Cδ (Li et al., 1998; Ren et al., 2002). MUC1 colocalizes with β-catenin in the nucleus (Baldus et al., 2004; Li et al., 2003a; Li et al., 2003c; Wen et al., 2003) and coactivates transcription of Wnt target genes (Huang et al., 2003). Other studies have shown that MUC1 also binds directly to p53 and regulates transcription of p53 target genes (Wei et al., 2005). Notably, overexpression of MUC1 is sufficient to induce anchorage-independent growth and tumorigenicity (Huang et al., 2003; Li et al., 2003b; Ren et al., 2002; Schroeder et al., 2004).

Most mitochondrial proteins are encoded in the nucleus and are imported into mitochondria by translocation complexes in the outer and inner mitochondrial membranes. Certain mitochondrial proteins contain N-terminal mitochondrial targeting sequences and interact with Tom20 in the outer mitochondrial membrane (Truscott et al., 2003). Other mitochondrial proteins contain internal targeting sequences and interact with the Tom70 receptor (Truscott et al., 2003). Recent work showed that mitochondrial proteins without internal targeting sequences are delivered to Tom70 by a complex of HSP70 and HSP90 (Young et al., 2003).

II. PI3-K AND SIGNALING

A. PI3-K

Phosphatidylinositol 3-kinases (PI3-kinases or PI3-Ks) are a family of enzymes involved in cellular functions such as cell growth, proliferation, differentiation, motility, survival and intracellular trafficking, which in turn are involved in cancer. In response to lipopolysaccharide, PI3-K phosphorylates p65, inducing anandamide synthesis to inhibit NF-κB activation. This is under the control of Fatty acid amide hydrolase (FAAH) limiting the ability of LPS to increase AEA levels and is also inhibited by wortmannin and cannabidiol, one of the only natural compounds to inhibit FAAH.

PI3-Ks are a family of related intracellular signal transducer enzymes capable of phosphorylating the 3 position hydroxyl group of the inositol ring of phosphatidylinositol (PtdIns). They are also known as phosphatidylinositol-3-kinases. The pathway, with oncogene PIK3CA and tumor suppressor PTEN (gene), is implicated in insensitivity of cancer tumors to insulin and IGF1, in calorie restriction. PI3-Ks interact with the IRS (insulin receptor substrate) in order to regulate glucose uptake through a series of phosphorylation events.

The phophoinositol-3-kinase family is divided into three different classes: Class I, Class II, and Class III. The classifications are based on primary structure, regulation, and in vitro lipid substrate specificity. Class I PI3-Ks are responsible for the production of Phosphatidylinositol 3-phosphate (PI(3)P), Phosphatidylinositol (3,4)-bisphosphate (PI(3,4)P2), and Phosphatidylinositol (3,4,5)-trisphosphate (PI(3,4,5)P3. The PI3-K is activated by G protein-coupled receptors and tyrosine kinase receptors. Class I PI3-K are heterodimeric molecules composed of a regulatory and a catalytic subunit; they are further divided between IA and IB subsets on sequence similarity. Class IA PI3-K is composed of a heterodimer between a p110 catalytic subunit and a p85 regulatory subunit. There are five variants of the p85 regulatory subunit, designated p85α, p55α, p50α, p85β, or p55γ. There are also three variants of the p110 catalytic subunit designated p110α, β, or δ catalytic subunit. The first three regulatory subunits are all splice variants of the same gene (Pik3r1), the other two being expressed by other genes (Pik3r2 and Pik3r3, p85β, and p55γ, respectively). The most highly expressed regulatory subunit is p85α; all three catalytic subunits are expressed by separate genes (Pik3ca, Pik3cb, and Pik3cd for p110α, p110β, and p110δ, respectively). The first two p110 isoforms (α and β) are expressed in all cells, but p110δ is expressed primarily in leukocytes, and it has been suggested that it evolved in parallel with the adaptive immune system. The regulatory p101 and catalytic p110γ subunits comprise the type IB PI3-K and are encoded by a single gene each. The p85 subunits contain SH2 and SH3 domains (Online 'Mendelian Inheritance in Man' (OMIM) 171833). The SH2 domains bind preferentially to phosphorylated tyrosine residues in the amino acid sequence context Y-X-X-M.

Class II and III PI3-K are differentiated from the Class I by their structure and function. Class II comprises three catalytic isoforms (C2α, C2β, and C2γ), but, unlike Classes I and III, no regulatory proteins. Class II catalyse the production of PI(3)P and PI(3,4)P2 from PI; however, little is known about their role in immune cells. C2α and C2β are expressed through the body, however expression of C2γ is limited to hepatocytes. The distinct feature of Class II PI3-Ks is the C-terminal C2 domain. This domain lacks critical Asp residues to coordinate binding of $Ca^{2+}$, which suggests class II PI3-Ks bind lipids in a $Ca^{2+}$-independent manner. Class III produces only PI(3)P from PI, but are more similar to Class I in structure, as they exist as a heterodimers of a catalytic (Vps34) and a regulatory (Vps15/p150) subunits. Class III seems to be primarily involved in the trafficking of proteins and vesicles. There is, however, evidence to show that they are able to contribute to the effectiveness of several process important to immune cells, not least phagocytosis.

The various 3-phosphorylated phosphoinositides that are produced by PI3-kinases (PtdIns3P, PtdIns(3,4)P2, PtdIns(3,5)P2, and PtdIns(3,4,5)P3) function in a mechanism by which an assorted group of signaling proteins, containing PX domain, pleckstrin homology domains (PH domains), FYVE domains and other phosphoinositide-binding domains, are recruited to various cellular membranes.

B. Signaling

PI3-kinases have been linked to an extraordinarily diverse group of cellular functions, including cell growth, proliferation, differentiation, motility, survival and intracellular trafficking. Many of these functions relate to the ability of class I PI3-kinases to activate protein kinase B (PKB, aka Akt) as in the PI3-K/AKT/mTOR pathway. The p110δ and p110γ isoforms regulate different aspects of immune responses. PI3-kinases are also a key component of the insulin signaling pathway. Hence there is great interest in the role of PI3-kinase signaling in diabetes mellitus.

The pleckstrin homology domain of AKT binds directly to PtdIns(3,4,5)P3 and PtdIns(3,4)P2, which are produced by activated PI 3-kinase. Since PtdIns(3,4,5)P3 and PtdIns(3,4)P2 are restricted to the plasma membrane, this results in translocation of AKT to the plasma membrane. Likewise, the phosphoinositide-dependent protein kinase 1 (PDK1 or, rarely referred to as PDPK1) also contains a pleckstrin homology domain that binds directly to PtdIns(3,4,5)P3 and PtdIns(3,4)P2, causing it to also translocate to the plasma membrane upon activation of PI 3-kinase. The colocalization of activated PDK1 and AKT allows AKT to become phosphorylated by PDK1 on threonine 308, leading to partial activation of AKT. Full activation of AKT occurs upon phosphorylation of serine 473 by the TORC2 complex of the mTOR protein kinase. (The nomenclature can be confusing. Note that PDK1 also refers to the unrelated enzyme Pyruvate dehydrogenase kinase, isozyme 1. Similarly, TORC2 also refers to the unrelated transcription factor Transducer of Regulated CREB activity 2, which has recently been renamed CREB-regulated transcription coactivator 2 (CRTC2) to reduce the confusion). The "PI3-k/AKT" signaling pathway has been shown to be required for an extremely diverse array of cellular activities—most notably cellular proliferation and survival. The phosphatidylinositol 3-kinase/protein kinase B pathway is stimulated in protection of astrocytes from ceramide-induced apoptosis.

Many other proteins have been identified that are regulated by PtdIns(3,4,5)P3, including Bruton's Tyrosine Kinase (BTK), General Receptor for Phosphoinositides-1 (GRP1), and the O-linked N-acetylglucosamine (O-GlcNAc) transferase. The class IA PI3-kinase p110α is mutated in many cancers. Many of these mutations cause the kinase to be more active. The PtdIns(3,4,5)P3 phosphatase PTEN that antagonizes PI 3-kinase signaling is absent from many tumors. Hence, PI3-kinase activity contributes significantly to cellular transformation and the development of cancer. For example, the PI3-K/AKT/mTOR pathway is important in apoptosis in, e.g., breast cancer and non-small-cell lung cancer. Indeed, mTOR is overactive in cancers and reduces apoptosis, thereby proliferation. Because PI3-K activation activates AKT, which in turn activates mTOR, these protein act in concert in the onocogenic process. Also, PI3-K may be overactive because PTEN is faulty or deficient.

III. PI3-K INHIBITORS

As discussed above, PI3-Ks are inhibited by wortmannin and cannabidiol. However, numerous other drugs are being developed for use as PI3-K inhibitors. Perifosine is currently in phase III clinical trials for colorectal cancer and multiple myeloma. Phase II candidates include CAL-101 and PX-866. Early stage candidates include BEZ235, SF1126 (for B-cell chronic lymphocytic leukemia), INK1117, IPI-145 (esp. for hematologic malignancies), GDC-0941, BKM120, XL147 (also known as SAR245408), XL765 (also known as SAR245409, Palomid 529, GSK1059615, ZSTK474, PWT33597 (for advanced solid tumors), IC87114, TG100-115, CAL263, PI-103, GNE-477, and CUDC-907.

In the examples below, the inhibitors LY294002 and GDC-0941 are used. LY 294002 (Mw: 307.34; Formula: $C_{19}H_{17}NO_3$) has been shown to be a potent inhibitor of PI3-kinase, acting as a competitive inhibitor for ATP binding site of the enzyme. LY294002 inhibits cell proliferation of many cancer cell lines and the ICs was observed between 10-25 μM. LY294002 is a pan PI3-kinase inhibitor as it inhibits all the isoforms of PI3-K. LY294002 also cause G1 arrest and is correlated to up-regulation of p27Kip1 and also inhibition of G1 CDKs in melanoma cells (Casagrande et al., 1998).

GDC-0941 (Mw: 513.64; Formula: $C_{23}H_{27}N_7O_3S_2$) is a PI3-kinase inhibitor with $IC_{50}$ ranges from 0.5 to 2 μM in different cell types (Folks et al., 2008). The orally bioavailable bismesylate salt is a potent small-molecule thieno[3,2-d]pyrimidine inhibitor of p100alpha and p100delta with potential antineoplastic activity. GDC-0941 selectively binds to PI3-K isoforms in an ATP-competitive manner, inhibiting the production of the secondary messenger phosphatidylinositol-3,4,5-trisphosphate (PIP3) and activation of the PI3-K/Akt signaling pathway; inhibition of tumor cell growth, motility and survival in susceptible tumor cell populations may result.

CAL-101 is an orally bioavailable, small molecule inhibitor of the delta isoform of the 110 kDa catalytic subunit of class I phosphoinositide-3 kinase (PI3-K) with potential immunomodulating and antineoplastic activities. Idelalisib inhibits the production of the second messenger phosphatidylinositol-3,4,5-trisphosphate (PIP3), preventing the activation of the PI3-K signaling pathway and inhibiting tumor cell proliferation, motility, and survival. Unlike other isoforms of PI3K, PI3K-delta is expressed primarily in hematopoietic lineages. The targeted inhibition of PI3K-delta is designed to preserve PI3K signaling in normal, non-neoplastic cells.

IV. THERAPIES

A. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15$^{th}$ Ed., 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Cancers

Oncogenesis is a multistep biological process, which is presently known to occur by the accumulation of genetic damage. On a molecular level, the process of tumorigenesis involves the disruption of both positive and negative regulatory effectors (Weinberg, 1989). The molecular basis for human carcinomas has been postulated to involve a number of oncogenes, tumor suppressor genes and repair genes. As discussed above, MUC has been identified as a major participant in aberrant signaling in abnormal cells, leading to cancer.

The present invention involves the treatment of cancer, in particular, those expressing MUC1. Thus, it is contemplated that a wide variety of tumors may be treated according to the present invention, including cancers of the brain, lung, liver, spleen, kidney, lymph node, pancreas, small intestine, blood cells, colon, stomach, breast, endometrium, prostate, testicle, ovary, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth to be slowed to some degree— indeed, any increase in patient comfort, function or longevity may be considered a successful treatment. Of course, it may be that the tumor growth is completely blocked or that some tumor regression is achieved. Clinical terminology such as "remission," "surgically resectable" and "reduction of tumor" burden also are contemplated given their normal usage.

C. Treatment Methods

PI3-K inhibitors can be administered to mammalian subjects (e.g., human patients) alone or in conjunction with other drugs that modulate inflammation. The compounds can also be administered to subjects that are genetically and/or due to, for example, physiological and/or environmental factors, or susceptible to cancer, e.g., subjects with a family history of cancer.

The dosage required depends on the choice of the route of administration; the nature of the formulation; the nature of the patient's disease; the subject's size, weight, surface area, age, and sex; other drugs being administered; and the judgment of the attending physician. Suitable dosages are in the range of 0.0001-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more times). Encapsulation of the polypeptide in a suitable delivery vehicle (e.g., polymeric microparticles or implantable devices) may increase the efficiency of delivery, particularly for oral delivery.

To treat cancers using the methods and compositions of the present invention, one will contact a target cell or subject with a PI3-K inhibitor and at least one other MUC1 therapy, in particular a MUC1 peptide therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the PI3-K inhibitor and the other includes the other agent.

Alternatively, the PI3-K inhibitor may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the eIF4A inhibitor or the other therapy will be desired. Various combinations may be employed, where the eIF4A inhibitor is "A," and the other therapy (e.g., MUC1 peptide therapy) is "B," as exemplified below:

```
A/B/A B/A/B B/B/A A/A/B B/A/A A/B/B B/B/B/A
B/B/A/B A/A/B/B A/B/A/B A/B/B/A B/B/A/A B/A/B/A
B/A/A/B B/B/B/A A/A/B/B B/A/A/A A/B/A/A A/A/B/A
A/B/B/B B/A/B/B B/B/A/B
```

Other combinations are contemplated, as discussed below.

Administration of the therapy or agents to a patient will follow general protocols for the treatment/administration of such compounds, taking into account the toxicity, if any, of the therapy. It is expected that the treatment cycles would be repeated as necessary. It also is contemplated that various standard cancer therapies, as well as surgical intervention, may be applied in combination with the described therapy.

The terms "contacted" and "exposed," when applied to a cell, are used herein to describe the process by which a PI3-K inhibitor and a MUC1 peptide are delivered to a target cell or are placed in direct juxtaposition with the target cell. To achieve cell killing or stasis, both agents are delivered to a cell in a combined amount effective to kill the cell or prevent it from dividing.

1. MUC1 Peptides

The structural features of MUC1 peptides according to the present invention are as follows. First, the peptides have no more than 20 consecutive residues of MUC1. Thus, the term "a peptide having no more than 20 consecutive residues," even when including the term "comprising," cannot be understood to comprise a greater number of consecutive MUC1 residues. Second, the peptides will contain the CQC motif, and may further comprise the CQCR (SEQ ID NO:49), CQCRR (SEQ ID NO:50), or CQCRRK (SEQ ID NO:4) motifs. Thus, the peptides will have, at a minimum, these four, five or six consecutive residues of the MUC1-C domain. Third, the peptides will have at least one amino acid residue attached to the NH$_2$-terminal side of the first C residue in the CQCRRK (SEQ ID NO:4) motif, such that the first C residue is "covered" by that at least one amino acid attached thereto. This residue may be native to MUC1 (i.e., from the transmembrane domain), may be selected at random (any of the twenty naturally-occurring amino acids or analogs thereof), or may be part of another peptide sequence (e.g., a tag sequence for purification, a stabilizing sequence, or a cell delivery domain).

In general, the peptides will be 50 residues or less, again, comprising no more than 20 consecutive residues of MUC1. The overall length may be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 residues. Ranges of peptide length of 4-50 residues, 7-50 residues, 4-25 residues 7-25, residues, 4-20 residues, 7-20 residues, and 3-15 residues, and 7-15 residues are contemplated. The number of consecutive MUC1 residues may be 3, 4, 5, 6, 7, 8, 9, 10, 11, 12, 13, 14, 15, 16, 17, 18, 19 or 20. Ranges of consecutive residues of 4-20 residues, 5-20 residues, 6-20 residues, 7-20 residues, 4-15 residues, 5-15 residues, 6-15 residues and 7-15 residues are contemplated.

The present invention may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

As mentioned above, the present invention contemplates fusing or conjugating a cell delivery domain (also called a cell delivery vector, or cell transduction domain). Such domains are well known in the art and are generally characterized as short amphipathic or cationic peptides and peptide derivatives, often containing multiple lysine and arginine resides (Fischer, 2007). Of particular interest are poly-D-Arg and poly-D-Lys sequences (e.g., dextrorotary residues, eight residues in length).

TABLE 1

| CDD/CTD PEPTIDES | SEQ ID NO |
|---|---|
| QAATATRGRSAASRPTERPRAPARSASRPRRPVE | 5 |
| RQIKIWFQNRRMKWKK | 6 |
| RRMKWKK | 7 |
| RRWRRWWRRWWRRWR | 8 |
| RGGRLSYSRRRFSTSTGR | 9 |
| YGRKKRRQRRR | 10 |
| RKKRRQRRR | 11 |
| YARAAARQARA | 12 |
| RRRRRRRR | 13 |

TABLE 1-continued

| CDD/CTD PEPTIDES | SEQ ID NO |
|---|---|
| KKKKKKKK | 14 |
| GWTLNSAGYLLGKINLKALAALAKXIL | 15 |
| LLILLRRRIRKQANAHSK | 16 |
| SRRHHCRSKAKRSRHH | 17 |
| NRARRNRRRVR | 18 |
| RQLRIAGRRLRGRSR | 19 |
| KLIKGRTPIKFGK | 20 |
| RRIPNRRPRR | 21 |
| KLALKLALKALKAALKLA | 22 |
| KLAKLAKKLAKLAK | 23 |
| GALFLGFLGAAGSTNGAWSQPKKKRKV | 24 |
| KETWWETWWTEWSQPKKKRKV | 25 |
| GALFLGWLGAAGSTMGAKKKRKV | 26 |
| MGLGLHLLVLAAALQGAKSKRKV | 27 |
| AAVALLPAVLLALLAPAAANYKKPKL | 28 |
| MANLGYWLLALFVTMWTDVGLCKKRPKP | 29 |
| LGTYTQDFNKFHTFPQTAIGVGAP | 30 |
| DPKGDPKGVTVTVTVTGKGDPXPD | 31 |
| PPPPPPPPPPPPPP | 32 |
| VRLPPPVRLPPVRLPPP | 33 |
| PRPLPPPRPG | 34 |
| SVRRRPRPPYLPRPRPPPFFPPRLPPRIPP | 35 |
| TRSSRAGLQFPVGRVHRLLRK | 36 |
| GIGKFLHSAKKFGKAFVGEIMNS | 37 |
| KWKLFKKIEKVGQNIRDGIIKAGPAVAVVGQATQIAK | 38 |
| ALWMTLLKKVLKAAAKAALNAVLVGANA | 39 |
| GIGAVLKVLTTGLPALISWIKRKRQQ | 40 |
| INLKALAALAKKIL | 41 |
| GFFALIPKIISSPLPKTLLSAVGSALGGSGGQE | 42 |
| LAKWALKQGFAKLKS | 43 |
| SMAQDIISTIGDLVKWIIQTVNXFTKK | 44 |
| LLGDFFRKSKEKIGKEFKRIVQRIKQRIKDFLANLVPRTES | 45 |
| LKKLLKKLLKKLLKKLLKKL | 46 |
| KLKLKLKLKLKLKLKLKL | 47 |
| PAWRKAFRWAWRMLKKAA | 48 |

Also as mentioned above, peptides modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino and/or carboxyl terminal residues.

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the twenty standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

In one aspect, the present invention focuses on peptides comprising the sequence CQCRRK (SEQ ID NO:4). Having identified this key structure in MUC1 oligomer formation, the inventor also contemplates that variants of the CQCRRK (SEQ ID NO:4) sequence may be employed. For example, certain non-natural amino acids that satisfy the structural constraints of the CQCRRK (SEQ ID NO:4) sequence may be substituted without a loss, and perhaps with an improvement in, biological function. In addition, the present inventor also contemplates that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

A particular modification is in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge that physically constrains the peptide into its native α-helical shape. In addition to helping retain the native structure needed to interact with a target molecule, this conformation also provides stability against peptidases as well as promotes cell-permeating properties.

More particularly, the term "peptide stapling" may encompasses the joining of two double bond-containing sidechains, two triple bond-containing sidechains, or one double bond-containing and one triple bond-containing side chain, which may be present in a polypeptide chain, using any number of reaction conditions and/or catalysts to facilitate such a reaction, to provide a singly "stapled" polypeptide. In a specific embodiment, the introduction of a staple entails a modification of standard peptide synthesis, with α-methyl, α-alkenyl amino acids being introduced at two positions along the peptide chain, separated by either three or six intervening residues (i+4 or i+7). These spacings place the stapling amino acids on the same fact of the α-helix, straddling either one (i+4) or two (i+7) helical turns. The fully elongated, resin-bound peptide can be exposed to a ruthenium catalyst that promotes cross-linking of the alkenyl chains through olefin metathesis, thereby forming an all-hydrocarbon macrocyclic cross-link. U.S. Pat. Nos. 7,192,713 and 7,183,059, and U.S. Patent Publications 2005/02506890 and 2006/0008848, describing this technology, are hereby incorporated by reference. See also Schafmeister et al. (2000); Walensky et al. (2004). Additionally, the term "peptide stitching" refers to multiple and tandem "stapling" events in a single peptide chain to provide a "stitched" (multiply stapled) polypeptide, each of which is incorporated herein by reference. See WO 2008/121767 for a specific example of stitched peptide technology.

2. Chemotherapeutics

PI3-K inhibitor/MUC1 peptide therapies may be further combined, advantageously, with conventional cancer therapies. These include one or more selected from the group of chemical or radiation based treatments and surgery. Chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etopoxside (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, or any analog or derivative variant of the foregoing.

Suitable therapeutic agents include, for example, vinca alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), serine kinase targeting agents, transitional metal complexes, proteasome inhibitors, antimetabolites (such as nucleoside analogs), alkylating agents, platinum-based agents, anthracycline antibiotics, topoisomerase inhibitors, macrolides, therapeutic antibodies, retinoids (such as all-trans retinoic acids or a derivatives thereof); geldanamycin or a derivative thereof (such as 17-AAG), and other standard chemotherapeutic agents well recognized in the art.

In some embodiments, the chemotherapeutic agent is any of (and in some embodiments selected from the group consisting of) adriamycin, colchicine, cyclophosphamide, actinomycin, bleomycin, daunorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, taxotere and derivatives thereof, and the like), topetecan, vinblastine, vincristine, tamoxifen, piposulfan, nab-5404, nab-5800, nab-5801, Irinotecan, HKP, Ortataxel, gemcitabine, HERCEPTIN® (trastuzumab), vinorelbine, DOXIL® (doxorubicin), capecitabine, GLEEVEC® (Imatinib), ALIMTA® (Pemetrexed), AVASTIN® (Bevacizumab), VELCADE® (Bortezomib), TARCEVA® (Erlotinib), NEULASTA® (Pegfilgrastim), Lapatinib, STI-571, ZD1839, IRESSA® (gefitinib), SH268, genistein, CEP2563, SU6668, SU11248, EMD121974, and Sorafenib.

In some embodiments, the chemotherapeutic agent is a composition comprising nanoparticles comprising a thiocolchicine derivative and a carrier protein (such as albumin).

In further embodiments, a combination of chemotherapeutic agents is administered to prostate cancer cells. The chemotherapeutic agents may be administered serially (within minutes, hours, or days of each other) or in parallel; they also may be administered to the patient in a pre-mixed single composition. The composition may or may not contain a glucocorticoid receptor antagonist. Combinations of prostate cancer therapeutics include, but are not limited to the following: AT (Adriamycin and Taxotere), AC±T: (Adriamycin and Cytoxan, with or without Taxol or Taxotere), CMF (Cytoxan, methotrexate, and fluorouracil), CEF (Cytoxan, Ellence, and fluorouracil), FAC (fluorouracil, Adriamycin, and Cytoxan), CAF (Cytoxan, Adriamycin, and fluorouracil) (the FAC and CAF regimens use the same medicines but use different doses and frequencies), TAC (Taxotere, Adriamycin, and Cytoxan), and GET (Gemzar, Ellence, and Taxol). In some embodiments trastuzumab (Herceptin®) is administered to a prostate cancer patient with a glucocorticoid receptor antagonist, which may be with or without a chemotherapeutic or a combination of chemotherapeutics.

The term "a serine/threonine kinase inhibitor," as used herein, relates to a compound which inhibits serine/threonine kinases. An example of a target of a serine/threonine kinase inhibitor includes, but is not limited to, dsRNA-dependent protein kinase (PKR). Examples of indirect targets of a serinelthreonine kinase inhibitor include, but are not limited to, MCP-1, NF-κB, elF2α, COX2, RANTES, IL8, CYP2A5, IGF-1, CYP2B, CYP2B2, CYP2H1, ALAS-1, HIF-1, erythropoietin and/or CYP1A. An example of a serine, theronine kinase inhibitor includes, but is not limited to, Sorafenib and 2-aminopurine, also known as 1-H-purin-2-amine(9CI). Sorafenib is marketed as NEXAVAR. The compounds can be used in combination with a glucocorticoid receptor antagonist.

The term "an angiogenesis inhibitor," as used herein, relates to a compound which targets, decreases or inhibits the production of new blood vessels. Targets of an angiogenesis inhibitor include, but are not limited to, methionine aminopeptidase-2 (MetAP-2), macrophage inflammatory protein-1 (MIP-1α), CCLS, TGF-β, lipoxygenase, cyclooxygenase, and topoisomerase. Indirect targets of an angiogenesis inhibitor include, but are not limited to, p21, p53, CDK2 and collagen synthesis. Examples of an angiogenesis inhibitor include, but are not limited to, Fumagillin, which is known as 2,4,6,8-decatetraenedioic acid, mono[3R,4S,5S,6R)-5-methoxy-4-[(2R,3R)-2-methyl-3-(3-methyl-2-butenyl)oxi-ranyl]-1-oxaspiro[2.5]oct-6-yl]ester, (2E,4E,6E,8E)-(9CI); Shikonin, which is also known as 1,4-naphthalenedione, 5,8-dihydroxy-2-[(1R)-1-hydroxy-4-methyl-3-pentenyl]-(9CI); Tranilast, which is also known as benzoic acid, 2-[[3-(3,4-dimethoxyphenyl)-1-oxo-2-propenyl]amino]-(9CI); ursolic acid; suramin; thalidomide and lenalidomide, and marketed as REVLIMID. The compounds can be used in combination with a glucocorticoid receptor antagonist.

3. Radiation

Radiation therapy that cause DNA damage and have been used extensively include what are commonly known as 7-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Laser therapy is the use of high-intensity light to destroy tumor cells. Laser therapy affects the cells only in the treated area. Laser therapy may be used to destroy cancerous tissue and relieve a blockage in the esophagus when the cancer cannot be removed by surgery. The relief of a blockage can help to reduce symptoms, especially swallowing problems. Photodynamic therapy (PDT), a type of laser therapy, involves the use of drugs that are absorbed by cancer cells; when exposed to a special light, the drugs become active and destroy the cancer cells. PDT may be used to relieve symptoms of esophageal cancer such as difficulty swallowing.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

4. Gene Therapy

Gene therapy is the insertion of polynucleotides, including DNA or RNA, into an individual's cells and tissues to treat a disease. Antisense therapy is also a form of gene therapy in the present invention. A therapeutic polynucleotide may be administered before, after, or at the same time of a first cancer therapy. Delivery of a vector encoding a variety of proteins is encompassed within the invention. For example, cellular expression of the exogenous tumor suppressor oncogenes would exert their function to inhibit excessive cellular proliferation, such as p53, p16, FHIT and C-CAM.

5. Other Agents

Additional agents to be used to improve the therapeutic efficacy of treatment include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon $\alpha$, $\beta$, and $\gamma$; IL-2 and other cytokines; F42K and other cytokine analogs; or MTP-1, MIP-1$\beta$, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

6. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue. Upon excision of part of all of cancerous cells, tissue, or tumor, a cavity may be formed in the body. Treatment may be accomplished by perfusion, direct injection or local application of the area with or without an additional anti-cancer therapy.

The skilled artisan is directed to "Remington's Pharmaceutical Sciences" 15$^{th}$ Ed., in particular pages 33:624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating cancers.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

GO-203-2C And PI3-K Inhibitors Induce Synergistic Killing of Breast Cancer Cells AlamarBlue Assay for Assessing Cell Viability.

alamarBlue assay involves the usage of a fluorometric/colorimetric growth indicator, alamarBlue based on the metabolic activity of cells. As cells grow, the innate metabolic activity results in a chemical reduction of alamarBlue. Continued growth maintains a reduced environment while inhibition of growth maintains an oxidized environment. Live cells cause the change of alamarBlue from oxidized (non-fluorescent, blue) form to reduced (fluorescent, red) form. Data can be collected using either fluorescence-based or absorbance-based instrumentation. Fluorescence is monitored at 530-560 nm excitation wavelength and at 590 nm emission wavelength. Absorbance is monitored at 570 am and 600 nm.

This assay was developed with a 96-well plate using ZR-75-1 or MCF-7 (breast carcinoma cell lines) or H1650 non-small cell lung carcinoma cells at different cell concentrations and the optimal cell number was calculated to be 5,000 cells/well in 100 ml volume. The cell number/well has to be optimized for each cell type to be tested. ZR-75-1 or MCF-7 cells were treated with various concentrations of GO-203-2c, LY294002 or GDC-0941 with 2-fold serial dilutions to obtain a total of 8 different concentrations. Cells in triplicate wells were treated with each concentration of GO-203-2c every day, for 4 days. On day 5, the medium in the plate was replaced with 10% alamarBlue solution and incubated for various time points (1-5 hrs). At the end of each hour, absorbance of the plate was measured at 570 nm and 600 nm as reference. A set of blank wells was maintained with medium alone and medium with alamarBlue for the purpose of calculating actual absorbance. Obtained absorbance values were plotted against respective concentrations of GO-2-3-2c.

Multiple cell lines were used first to define the IC50s of GO-203-2c and PI3-K inhibitors. The pan inhibitor of PI3-K, LY294002 and PI3-Ka specific inhibitor GDC-0941 were used in these studies. Alamar blue assays were performed to determine cell proliferations when treated with GO-203-2c and PI3-K inhibitors either alone or in combination.

Results.

FIG. 1 (H-1650 cells) show plots obtained for one of the assays performed with GO-203-2c as the killing agent using H-1650 cell line with the above mentioned conditions. In this plot, A and D represent the values of the upper and lower asymptotes and B is the slope and C is the midpoint of the curve. C, being the mid point of the curve, can be used for deducing the $LD_{50}$ of the reagent under test. Accordingly, the data presented here shows the percent reduction of alamarBlue is 55.65% at the lowest concentration tested (0.078 mM) which is equivalent to the untreated cell control (55.34% reduction, 100% cell viability) and the highest concentration tested (10 mM) yields 6.86% reduction of alamarBlue which indicates 12.3% of live cells at 10 mM. Analysis of standard curve shows that 27.67% reduction of alamarBlue at 50% killing of cells that is achieved with 2.294 mM of GO-203-2C which is indicated by the C value. Therefore, the $LD_{50}$ value for GO-203-2c is 2.294 mM in this particular experiment.

ZR-75-1 or MCF-7 breast carcinoma cells were separately treated with different concentrations of LY294002 or GDC-0941. Alamar assays were performed to calculate the IC50 of each drug in both cell types. Similar experiments were performed with GO-203-2C (as described above). Following obtaining the $IC_{50}$s for GO-203-2C, LY294002 or GDC-0941, ZR-75-1 or MCF-7 cells were treated with different doses of GO-203-2C, LY294002 or GDC-0941 stand alone as well as in combinations. Alamar assays were performed and the data was analyzed using CALCUSYN® Software (analyzer of combined drug efficacy). Dose-response curves were plotted for different drugs in both the cell types. Isobologram analysis of the data demonstrated synergy between GO-203-2C and LY294002 or GDC-0941 (FIGS. 2-9).

A further example will utilize the PI3-K delta inhibitor CAL-101 in combination with GO-203-2C for hematologic malignancies, such as acute myelogenous leukemia.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. REFERENCES

The following references, to the extent that they provide exemplary procedural or other details supplementary to those set forth herein, are specifically incorporated herein by reference:

U.S. Pat. No. 5,440,013
U.S. Pat. No. 5,446,128
U.S. Pat. No. 5,475,085
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,840,833
U.S. Pat. No. 5,859,184
U.S. Pat. No. 5,929,237
U.S. Pat. No. 6,261,569
U.S. Pat. No. 7,183,059
U.S. Pat. No. 7,192,713
U.S. Patent Appln. 2005/02506890
U.S. Patent Appln. 2006/0008848
Ahmad et al., *Cancer Res.*, 69:7013-7021, 2009.
Ahmad et al., *Science Signaling*, 4(160):ra9, 2011.
Baldus et al., *Clin. Cancer Res.*, 10(8):2790-2796, 2004.
Bodanszky et al., *J. Antibiot.*, 29(5):549-53, 1976.
Casagrande et al., *FEBS Letters*, 422:385-390, 1998.
Fischer, *Med. Res. Rev.* 27(6):755-796, 2007.
Folks et al., *J. Med. Chem.*, 51: 5522-5532, 2008.
Gendler et al., *J. Biol. Chem.*, 263:12820-12823, 1988.
Huang et al., *Cancer Biol Ther.*, 2:702-706, 2003.
Huang et al. *Cancer Res.*, 65:10413-10422, 2005.
Johnson et al., In: *Biotechnology And Pharmacy*, Pezzuto et al. (Eds.), Chapman and Hall, NY, 1993.
Joshi et al., *Mol. Cancer Ther.*, 8:3056-3065, 2009.
Kinlough et al., *J. Biol. Chem.*, 279(51):53071-53077, 2004.
Kufe et al., *Hybridoma*, 3:223-232, 1984.
Kufe, *Nat. Rev. Cancer* 9:874-885, 2009.
Levitan et al. *J. Biol. Chem.*, 280:33374-33386, 2005.
Li et al., *Oncogene*, 22:6107-6110, 2003a.
Li et al., *Cancer Biol. Ther.*, 2:187-193, 2003b.
Li et al. *Mol. Cancer Res.*, 1:765-775, 2003c.
Li et al., *J. Biol. Chem.*, 276:35239-35242, 2001a.
Li et al, *J. Biol. Chem.*, 276:6061-6064, 2001b.
Li et al., *Oncogene*, 22:6107-6110, 2003.
Li et al., *Mol. Cell Biol.*, 18:7216-7224, 1998.
Ligtenberg et al., *J. Biol. Chem.*, 267, 6171-6177, 1992.
Merlo et al., *Cancer Res.*, 49, 6966-6971, 1989.
Merrifield, *J. Am. Chem. Soc.*, 85:2149-2154, 1963.
PCT Appln. WO 08/121,767
Peptide Synthesis, 1985
Perey et al., *Cancer Res.*, 52(22):6365-6370, 1992.
Protective Groups in Organic Chemistry, 1973
Raina et al., *Cancer Res.* 69:5133-5141, 2009.
Raina et al., *J. Biol. Chem.*, 279:20607-20612, 2004.
Raina et al., *Mol. Cancer Therapeutics*, 10:806-816, 2011.
Ramasamy et al., *Mol. Cell*, 27:992-1004, 2007.
Remington's Pharmaceutical Sciences, 15th Ed., 1035-1038 and 1570-1580, 1990.
Remington's Pharmaceutical Sciences, 15th Ed., 33:624-652, 1990.
Ren et al, *Cancer Cell*, 5:163-175, 2004.
Ren et al., *J. Biol. Chem.*, 277:17616-17622, 2002.
Schafmeister et al., *J. Amer. Chem. Soc.*, 122(24): 5891-5892, 2000.
Schroeder et al., *J. Biol. Chem.*, 276(16):13057-13064 2001.
Siddiqui et al., *Proc. Natl. Acad. Sci. USA*, 85:2320-2323, 1988.
Solid Phase Peptide Synthelia, 1984
Truscott et al., *J Cell Biol.*, 163(4):707-713, 2003.
Walensky et al., *Science* 305:1466-1470, 2004.
Wei et al., *Cancer Cell*, 7:167-178, 2005.
Weinberg, *Ciba Found Symp.*, 142:99-105, 1989.

Wen et al, *J. Biol. Chem.*, 278:38029-38039, 2003.
Yamamoto et al., *J. Biol. Chem.*, 272:12492-12494, 1997.
Yin and Kufe, *J. Biol. Chem.*, 278:35458-35464, 2003.
Yin et al., *J. Biol. Chem.* 282:257-266, 2007.
Young et al. *Cell.* 112(1):41-50, 2003.
Zhou et al., *Mol. Pharm.*, 79:886-893, 2011.

The invention claimed is:

1. A method of inhibiting a cancer cell that expresses mucin 1 (MUC1) comprising contacting said cancer cell with a pharmaceutical composition comprising (a) an inhibitor of phosphatidylinositol 3-kinase (PI3-K) and (b) a MUC1 peptide of at least 4 consecutive MUC1 residues and no more than 20 consecutive MUC1 residues and comprising the sequence CQC, wherein the amino-terminal cysteine of CQC is covered on its $NH_2$-terminus by at least one amino acid residue that need not correspond to the native MUC1 transmembrane sequence.

2. The method of claim 1, wherein said cancer cell is metastatic, recurrent or multidrug resistant cancer cell.

3. The method of claim 1, further comprising contacting said cancer cell with said PI3-K inhibitor more than once.

4. The method of claim 1, further comprising contacting said cancer cell with said peptide more than once.

5. The method of claim 1, further comprising contacting said cancer cell with said PI3-K inhibitor and said peptide more than once.

6. The method of claim 1, wherein said PI3-K inhibitor is a PI3-K Class I inhibitor.

7. The method of claim 1, wherein said PI3-K inhibitor is a PI3-K Class I-selective or PI3-K Class I-specific inhibitor.

8. The method of claim 1, wherein said cancer cell is a carcinoma cell, a leukemia cell or a myeloma cell.

9. The method of claim 7, wherein the carcinoma cell is a prostate or breast carcinoma cell.

10. The method of claim 1, wherein said peptide comprises at least 6, 7 or 8 consecutive MUC1 residues, comprising CQCRRK (SEQ ID NO:4).

11. The method of claim 1, wherein said peptide contains no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1.

12. The method of claim 1, wherein said peptide is fused to a cell delivery domain.

13. The method of claim 12, wherein said cell delivery domain is poly-D-R, poly-D-P or poly-D-K.

14. The method of claim 1, wherein said peptide comprises all L amino acids or all D amino acids.

15. The method of claim 1, wherein said peptide comprises a mix of L and D amino acids.

* * * * *

SEQUENCE LISTING

```
<160> NUMBER OF SEQ ID NOS: 65

<210> SEQ ID NO 1
<211> LENGTH: 366
<212> TYPE: PRT
<213> ORGANISM: Mus musculus

<400> SEQUENCE: 1

Met Thr Pro Gly Thr Gln Ser Pro Phe Phe Leu Leu Leu Leu Leu Thr
1               5                   10                  15

Val Leu Thr Ala Thr Thr Ala Pro Lys Pro Ala Thr Val Val Gly Ser
                20                  25                  30

Val Val Val Gln Leu Thr Leu Ala Phe Arg Glu Gly Thr Ile Asn Val
            35                  40                  45

His Asp Val Glu Thr Gln Phe Asn Gln Tyr Lys Thr Glu Ala Ala Ser
        50                  55                  60

Arg Tyr Asn Leu Thr Ile Ser Asp Val Ser Val Ser Asp Val Pro Phe
65                  70                  75                  80

Pro Phe Ser Ala Gln Ser Gly Ala Gly Gly Gly Gly Ser Gly Gly
                85                  90                  95

Gly Gly Ser Gly Gly Gly Ser Lys Leu Glu Pro Arg Gly Pro Thr
                100                 105                 110

Ile Lys Pro Cys Pro Pro Cys Lys Cys Pro Gly Lys Ser Leu Asp Gln
                115                 120                 125

Ser Ser Thr Pro Gly Arg Met Val Ser Ala Ile Asn Ile Pro Ala Leu
        130                 135                 140

Glu Asp Lys Pro Cys Thr Asp Pro Phe Pro Ser Leu Leu Ile Ser Thr
145                 150                 155                 160

Pro Arg Gly Trp Thr Ile Arg Leu His Leu Pro Ser Lys Asp Gln Gly
                165                 170                 175

Cys Thr His Asp Leu Pro Glu Pro His Ser His Met Cys Gly Gly Gly
                180                 185                 190

Cys Glu Arg Gly Pro Arg Cys Pro Asp Gln Leu Val Cys Glu Gln Arg
            195                 200                 205

Gly Ser Thr His Ser Ser Asp Thr Asn Pro Arg Gly Leu Gln Gln Tyr
        210                 215                 220

Ser Pro Gly Gly Gln Cys Pro Pro His Pro Ala Pro Gly Leu Asp Glu
225                 230                 235                 240

Trp Gln Gly Phe Arg Met Arg Arg Gln Gln Arg Pro Pro Ser Ala
                245                 250                 255

His Arg Glu Asn His Leu Lys Thr Gln Arg Glu Leu Gln Pro Asp Cys
                260                 265                 270

Met Gly Ala Gly Met Gly Ile Arg Ile Lys Val Cys Val Asp Ser Leu
            275                 280                 285

Leu Leu Gln Pro Pro Leu Tyr Met Phe Leu Pro Ser Gln Gly Gln Glu
        290                 295                 300

Leu His Arg Tyr Met Ser Cys Leu His Gln Arg Lys Arg Leu Arg Asn
305                 310                 315                 320

Arg Ser Leu Pro Ala Trp Ser Gln Thr Ser Cys Leu Lys Thr Phe Thr
                325                 330                 335

Trp Ser Gly Pro Thr Thr Gly Lys Gln Ser Thr Thr Arg Thr Leu Asn
```

```
                340             345             350
Gln Ser Trp Thr Leu Met Val Leu Thr Ser Cys Thr Ala Ser
        355             360             365

<210> SEQ ID NO 2
<211> LENGTH: 159
<212> TYPE: PRT
<213> ORGANISM: Homo sapiens

<400> SEQUENCE: 2

Gly Ser Val Val Val Gln Leu Thr Leu Ala Phe Arg Glu Gly Thr Ile
1               5                   10                  15

Asn Val His Asp Val Glu Thr Gln Phe Asn Gln Tyr Lys Thr Glu Ala
                20                  25                  30

Ala Ser Arg Tyr Asn Leu Thr Ile Ser Asp Val Ser Val Ser Asp Val
            35                  40                  45

Pro Phe Pro Phe Ser Ala Gln Ser Gly Ala Gly Val Pro Gly Trp Gly
        50                  55                  60

Ile Ala Leu Leu Val Leu Val Cys Val Leu Val Ala Leu Ala Ile Val
65                  70                  75                  80

Tyr Leu Ile Ala Leu Ala Val Cys Gln Cys Arg Arg Lys Asn Tyr Gly
                85                  90                  95

Gln Leu Asp Ile Phe Pro Ala Arg Asp Thr Tyr His Pro Met Ser Glu
            100                 105                 110

Tyr Pro Thr Tyr His Thr His Gly Arg Tyr Val Pro Pro Ser Ser Thr
        115                 120                 125

Asp Arg Ser Pro Tyr Glu Lys Val Ser Ala Gly Asn Gly Gly Ser Ser
    130                 135                 140

Leu Ser Tyr Thr Asn Pro Ala Val Ala Ala Thr Ser Ala Asn Leu
145                 150                 155

<210> SEQ ID NO 3
<211> LENGTH: 15
<212> TYPE: PRT
<213> ORGANISM: Homo sapiens

<400> SEQUENCE: 3

Cys Gln Cys Arg Arg Lys Asn Tyr Gly Gln Leu Asp Ile Phe Pro
1               5                   10                  15

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Cys Gln Cys Arg Arg Lys
1               5

<210> SEQ ID NO 5
<211> LENGTH: 34
<212> TYPE: PRT
<213> ORGANISM: Artificial Sequence
<220> FEATURE:
<223> OTHER INFORMATION: Synthetic peptide

<400> SEQUENCE: 5

Gln Ala Ala Thr Ala Thr Arg Gly Arg Ser Ala Ala Ser Arg Pro Thr
1               5                   10                  15
```

```
Glu Arg Pro Arg Ala Pro Ala Arg Ser Ala Ser Arg Pro Arg Arg Pro
            20                  25                  30

Val Glu

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Arg Arg Met Lys Trp Lys Lys
1               5

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

Arg Arg Trp Arg Arg Trp Trp Arg Arg Trp Trp Arg Arg Trp Arg Arg
1               5                   10                  15

<210> SEQ ID NO 9
<211> LENGTH: 18
<212> TYPE: PRT
<213> ORGANISM: Artificial Sequence
<220> FEATURE:
<223> OTHER INFORMATION: Synthetic peptide

<400> SEQUENCE: 9

Arg Gly Gly Arg Leu Ser Tyr Ser Arg Arg Arg Phe Ser Thr Ser Thr
1               5                   10                  15

Gly Arg

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

Tyr Gly Arg Lys Lys Arg Arg Gln Arg Arg
1               5                   10

<210> SEQ ID NO 11
<211> LENGTH: 9
<212> TYPE: PRT
<213> ORGANISM: Artificial Sequence
<220> FEATURE:
```

<223> OTHER INFORMATION: Synthetic peptide

<400> SEQUENCE: 11

Arg Lys Lys Arg Arg Gln Arg Arg Arg
1               5

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12

Tyr Ala Arg Ala Ala Ala Arg Gln Ala Arg Ala
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Arg Arg Arg Arg Arg Arg Arg Arg
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide

<400> SEQUENCE: 14

Lys Lys Lys Lys Lys Lys Lys Lys
1               5

<210> SEQ ID NO 15
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 15

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25

<210> SEQ ID NO 16
<211> LENGTH: 18
<212> TYPE: PRT
<213> ORGANISM: Artificial Sequence
<220> FEATURE:
<223> OTHER INFORMATION: Synthetic peptide

<400> SEQUENCE: 16

Leu Leu Ile Leu Leu Arg Arg Arg Ile Arg Lys Gln Ala Asn Ala His
1               5                   10                  15

Ser Lys

<210> SEQ ID NO 17
<211> LENGTH: 16
<212> TYPE: PRT
<213> ORGANISM: Artificial Sequence
<220> FEATURE:
<223> OTHER INFORMATION: Synthetic peptide

<400> SEQUENCE: 17

Ser Arg Arg His His Cys Arg Ser Lys Ala Lys Arg Ser Arg His His
1               5                   10                  15

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide

<400> SEQUENCE: 18

Asn Arg Ala Arg Arg Asn Arg Arg Arg Val Arg
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Arg Gln Leu Arg Ile Ala Gly Arg Arg Leu Arg Gly Arg Ser Arg
1               5                   10                  15

<210> SEQ ID NO 20
<211> LENGTH: 13
<212> TYPE: PRT
<213> ORGANISM: Artificial Sequence
<220> FEATURE:
<223> OTHER INFORMATION: Synthetic peptide

<400> SEQUENCE: 20

Lys Leu Ile Lys Gly Arg Thr Pro Ile Lys Phe Gly Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic peptide

<400> SEQUENCE: 21

Arg Arg Ile Pro Asn Arg Arg Pro Arg Arg
1               5                   10

<210> SEQ ID NO 22
<211> LENGTH: 18
<212> TYPE: PRT
<213> ORGANISM: Artificial Sequence
<220> FEATURE:
<223> OTHER INFORMATION: Synthetic peptide

<400> SEQUENCE: 22

Lys Leu Ala Leu Lys Leu Ala Leu Lys Ala Leu Lys Ala Ala Leu Lys
1               5                   10                  15

Leu Ala

<210> SEQ ID NO 23
<211> LENGTH: 14
<212> TYPE: PRT
<213> ORGANISM: Artificial Sequence
<220> FEATURE:
<223> OTHER INFORMATION: Synthetic peptide

<400> SEQUENCE: 23

Lys Leu Ala Lys Leu Ala Lys Lys Leu Ala Lys Leu Ala Lys
1               5                   10

<210> SEQ ID NO 24
<211> LENGTH: 27
<212> TYPE: PRT
<213> ORGANISM: Artificial Sequence
<220> FEATURE:
<223> OTHER INFORMATION: Synthetic peptide

<400> SEQUENCE: 24

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25

<210> SEQ ID NO 25
<211> LENGTH: 21
<212> TYPE: PRT
<213> ORGANISM: Artificial Sequence
<220> FEATURE:
<223> OTHER INFORMATION: Synthetic peptide

<400> SEQUENCE: 25

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 26
<211> LENGTH: 23
<212> TYPE: PRT
<213> ORGANISM: Artificial Sequence
<220> FEATURE:
<223> OTHER INFORMATION: Synthetic peptide

<400> SEQUENCE: 26

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 27
<211> LENGTH: 23
<212> TYPE: PRT
<213> ORGANISM: Artificial Sequence
<220> FEATURE:
<223> OTHER INFORMATION: Synthetic peptide

<400> SEQUENCE: 27

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 28
<211> LENGTH: 26
<212> TYPE: PRT
<213> ORGANISM: Artificial Sequence
<220> FEATURE:
<223> OTHER INFORMATION: Synthetic peptide

<400> SEQUENCE: 28

Ala Ala Val Ala Leu Leu Pro Ala Val Leu Leu Ala Leu Leu Ala Pro
1               5                   10                  15

Ala Ala Ala Asn Tyr Lys Lys Pro Lys Leu
            20                  25

<210> SEQ ID NO 29
<211> LENGTH: 28
<212> TYPE: PRT
<213> ORGANISM: Artificial Sequence
<220> FEATURE:
<223> OTHER INFORMATION: Synthetic peptide

<400> SEQUENCE: 29

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 30
<211> LENGTH: 24
<212> TYPE: PRT
<213> ORGANISM: Artificial Sequence
<220> FEATURE:
<223> OTHER INFORMATION: Synthetic peptide

<400> SEQUENCE: 30

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 31
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 31

Asp Pro Lys Gly Asp Pro Lys Gly Val Thr Val Thr Val Thr Val Thr
1               5                   10                  15

Val Thr Gly Lys Gly Asp Pro Xaa Pro Asp
            20                  25

<210> SEQ ID NO 32
<211> LENGTH: 14
<212> TYPE: PRT
<213> ORGANISM: Artificial Sequence
<220> FEATURE:
<223> OTHER INFORMATION: Synthetic peptide

<400> SEQUENCE: 32

```
Pro Pro Pro Pro Pro Pro Pro Pro Pro Pro Pro Pro
1               5                   10
```

<210> SEQ ID NO 33
<211> LENGTH: 18
<212> TYPE: PRT
<213> ORGANISM: Artificial Sequence
<220> FEATURE:
<223> OTHER INFORMATION: Synthetic peptide

<400> SEQUENCE: 33

```
Val Arg Leu Pro Pro Val Arg Leu Pro Pro Val Arg Leu Pro
1               5                   10                  15

Pro Pro
```

<210> SEQ ID NO 34
<211> LENGTH: 10
<212> TYPE: PRT
<213> ORGANISM: Artificial Sequence
<220> FEATURE:
<223> OTHER INFORMATION: Synthetic peptide

<400> SEQUENCE: 34

```
Pro Arg Pro Leu Pro Pro Pro Arg Pro Gly
1               5                   10
```

<210> SEQ ID NO 35
<211> LENGTH: 30
<212> TYPE: PRT
<213> ORGANISM: Artificial Sequence
<220> FEATURE:
<223> OTHER INFORMATION: Synthetic peptide

<400> SEQUENCE: 35

```
Ser Val Arg Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
            20                  25                  30
```

<210> SEQ ID NO 36
<211> LENGTH: 21
<212> TYPE: PRT
<213> ORGANISM: Artificial Sequence
<220> FEATURE:
<223> OTHER INFORMATION: Synthetic peptide

<400> SEQUENCE: 36

```
Thr Arg Ser Ser Arg Ala Gly Leu Gln Phe Pro Val Gly Arg Val His
1               5                   10                  15

Arg Leu Leu Arg Lys
            20
```

<210> SEQ ID NO 37
<211> LENGTH: 23
<212> TYPE: PRT
<213> ORGANISM: Artificial Sequence
<220> FEATURE:
<223> OTHER INFORMATION: Synthetic peptide

<400> SEQUENCE: 37

```
Gly Ile Gly Lys Phe Leu His Ser Ala Lys Lys Phe Gly Lys Ala Phe
1               5                   10                  15

Val Gly Glu Ile Met Asn Ser
            20
```

```
<210> SEQ ID NO 38
<211> LENGTH: 37
<212> TYPE: PRT
<213> ORGANISM: Artificial Sequence
<220> FEATURE:
<223> OTHER INFORMATION: Synthetic peptide

<400> SEQUENCE: 38

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Gly Gln Ala
            20                  25                  30

Thr Gln Ile Ala Lys
        35

<210> SEQ ID NO 39
<211> LENGTH: 28
<212> TYPE: PRT
<213> ORGANISM: Artificial Sequence
<220> FEATURE:
<223> OTHER INFORMATION: Synthetic peptide

<400> SEQUENCE: 39

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25

<210> SEQ ID NO 40
<211> LENGTH: 26
<212> TYPE: PRT
<213> ORGANISM: Artificial Sequence
<220> FEATURE:
<223> OTHER INFORMATION: Synthetic peptide

<400> SEQUENCE: 40

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 41
<211> LENGTH: 14
<212> TYPE: PRT
<213> ORGANISM: Artificial Sequence
<220> FEATURE:
<223> OTHER INFORMATION: Synthetic peptide

<400> SEQUENCE: 41

Ile Asn Leu Lys Ala Leu Ala Ala Leu Ala Lys Lys Ile Leu
1               5                   10

<210> SEQ ID NO 42
<211> LENGTH: 33
<212> TYPE: PRT
<213> ORGANISM: Artificial Sequence
<220> FEATURE:
<223> OTHER INFORMATION: Synthetic peptide

<400> SEQUENCE: 42

Gly Phe Phe Ala Leu Ile Pro Lys Ile Ile Ser Ser Pro Leu Pro Lys
1               5                   10                  15

Thr Leu Leu Ser Ala Val Gly Ser Ala Leu Gly Gly Ser Gly Gly Gln
            20                  25                  30
```

Glu

<210> SEQ ID NO 43
<211> LENGTH: 15
<212> TYPE: PRT
<213> ORGANISM: Artificial Sequence
<220> FEATURE:
<223> OTHER INFORMATION: Synthetic peptide

<400> SEQUENCE: 43

Leu Ala Lys Trp Ala Leu Lys Gln Gly Phe Ala Lys Leu Lys Ser
1               5                   10                  15

<210> SEQ ID NO 44
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(23)
<223> OTHER INFORMATION: Xaa can be any naturally occurring amino acid

<400> SEQUENCE: 44

Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25

<210> SEQ ID NO 45
<211> LENGTH: 41
<212> TYPE: PRT
<213> ORGANISM: Artificial Sequence
<220> FEATURE:
<223> OTHER INFORMATION: Synthetic peptide

<400> SEQUENCE: 45

Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
            20                  25                  30

Ala Asn Leu Val Pro Arg Thr Glu Ser
        35                  40

<210> SEQ ID NO 46
<211> LENGTH: 20
<212> TYPE: PRT
<213> ORGANISM: Artificial Sequence
<220> FEATURE:
<223> OTHER INFORMATION: Synthetic peptide

<400> SEQUENCE: 46

Leu Lys Lys Leu Leu Lys Lys Leu Leu Lys Lys Leu Leu Lys Lys Leu
1               5                   10                  15

Leu Lys Lys Leu
            20

<210> SEQ ID NO 47
<211> LENGTH: 18
<212> TYPE: PRT
<213> ORGANISM: Artificial Sequence
<220> FEATURE:
<223> OTHER INFORMATION: Synthetic peptide

```
<400> SEQUENCE: 47

Lys Leu Lys Leu Lys Leu Lys Leu Lys Leu Lys Leu Lys Leu
1               5                   10                  15

Lys Leu

<210> SEQ ID NO 48
<211> LENGTH: 18
<212> TYPE: PRT
<213> ORGANISM: Artificial Sequence
<220> FEATURE:
<223> OTHER INFORMATION: Synthetic peptide

<400> SEQUENCE: 48

Pro Ala Trp Arg Lys Ala Phe Arg Trp Ala Trp Arg Met Leu Lys Lys
1               5                   10                  15

Ala Ala

<210> SEQ ID NO 49
<211> LENGTH: 4
<212> TYPE: PRT
<213> ORGANISM: Artificial Sequence
<220> FEATURE:
<223> OTHER INFORMATION: Synthetic peptide

<400> SEQUENCE: 49

Cys Gln Cys Arg
1

<210> SEQ ID NO 50
<211> LENGTH: 5
<212> TYPE: PRT
<213> ORGANISM: Artificial Sequence
<220> FEATURE:
<223> OTHER INFORMATION: Synthetic peptide

<400> SEQUENCE: 50

Cys Gln Cys Arg Arg
1               5

<210> SEQ ID NO 51
<211> LENGTH: 19
<212> TYPE: PRT
<213> ORGANISM: Artificial Sequence
<220> FEATURE:
<223> OTHER INFORMATION: Synthetic peptide

<400> SEQUENCE: 51

Ala Ile Val Tyr Leu Ile Ala Leu Ala Val Cys Gln Cys Arg Arg Lys
1               5                   10                  15

Asn Tyr Gly

<210> SEQ ID NO 52
<211> LENGTH: 17
<212> TYPE: PRT
<213> ORGANISM: Artificial Sequence
<220> FEATURE:
<223> OTHER INFORMATION: Synthetic peptide

<400> SEQUENCE: 52

Ala Ile Val Tyr Leu Ala Leu Ala Cys Gln Cys Arg Arg Lys Asn Tyr
1               5                   10                  15

Gly
```

```
<210> SEQ ID NO 53
<211> LENGTH: 15
<212> TYPE: PRT
<213> ORGANISM: Artificial Sequence
<220> FEATURE:
<223> OTHER INFORMATION: Synthetic peptide

<400> SEQUENCE: 53

Ala Lys Lys Tyr Leu Ala Leu Ala Cys Gln Cys Arg Lys Asn Tyr
1               5                   10                  15

<210> SEQ ID NO 54
<211> LENGTH: 24
<212> TYPE: PRT
<213> ORGANISM: Artificial Sequence
<220> FEATURE:
<223> OTHER INFORMATION: Synthetic peptide

<400> SEQUENCE: 54

Arg Arg Arg Arg Arg Arg Arg Arg Cys Gln Cys Arg Arg Lys Asn
1               5                   10                  15

Tyr Gly Gln Leu Asp Ile Phe Pro
            20

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide

<400> SEQUENCE: 55

Cys Gln Cys Arg Arg Lys Asn
1               5

<210> SEQ ID NO 56
<211> LENGTH: 11
<212> TYPE: PRT
<213> ORGANISM: Artificial Sequence
<220> FEATURE:
<223> OTHER INFORMATION: Synthetic peptide

<400> SEQUENCE: 56

Arg Arg Arg Cys Gln Cys Arg Arg Lys Asn Arg
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthetic peptide

<400> SEQUENCE: 57

Arg Arg Cys Gln Cys Arg Arg Lys Asn Arg
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Synthetic peptide

<400> SEQUENCE: 58

Arg Arg Cys Gln Cys Arg Arg Lys Asn
1               5
```

```
<210> SEQ ID NO 59
<211> LENGTH: 16
<212> TYPE: PRT
<213> ORGANISM: Artificial Sequence
<220> FEATURE:
<223> OTHER INFORMATION: Synthetic peptide

<400> SEQUENCE: 59

Cys Gln Cys Arg Arg Lys Asn Arg Arg Arg Arg Arg Arg Arg Arg Arg
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Synthetic peptide

<400> SEQUENCE: 60

Arg Arg Arg Arg Arg Arg Arg Arg Arg Asn Lys Arg Arg Cys Gln Cys
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Synthetic peptide

<400> SEQUENCE: 61

Asn Lys Arg Arg Cys Gln Cys Arg Arg Arg Arg Arg Arg Arg Arg Arg
1               5                   10                  15

<210> SEQ ID NO 62
<211> LENGTH: 12
<212> TYPE: PRT
<213> ORGANISM: Artificial Sequence
<220> FEATURE:
<223> OTHER INFORMATION: Synthetic peptide

<400> SEQUENCE: 62

Arg Arg Arg Arg Arg Arg Arg Arg Arg Cys Gln Cys
1               5                   10

<210> SEQ ID NO 63
<211> LENGTH: 16
<212> TYPE: PRT
<213> ORGANISM: Artificial Sequence
<220> FEATURE:
<223> OTHER INFORMATION: Synthetic peptide

<400> SEQUENCE: 63

Arg Arg Arg Arg Arg Arg Arg Arg Arg Asn Lys Arg Arg Cys Gln Cys
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Synthetic peptide

<400> SEQUENCE: 64

Arg Arg Arg Arg Arg Arg Arg Arg Arg Ala Gln Ala Arg Arg Lys Asn
1               5                   10                  15
```

```
<210> SEQ ID NO 65
<211> LENGTH: 69
<212> TYPE: PRT
<213> ORGANISM: Artificial Sequence
<220> FEATURE:
<223> OTHER INFORMATION: Synthetic peptide

<400> SEQUENCE: 65

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
            20                  25                  30

Gly Arg Tyr Val Pro Pro Ser Ser Thr Asp Arg Ser Pro Tyr Glu Lys
            35                  40                  45

Val Ser Ala Gly Asn Gly Gly Ser Ser Leu Tyr Thr Asn Pro Ala Val
    50                  55                  60

Ala Ala Ala Ser Leu
65
```